US011357612B2

(12) United States Patent
Shipley et al.

(10) Patent No.: US 11,357,612 B2
(45) Date of Patent: Jun. 14, 2022

(54) STENT GRAFT WITH SACRIFICIAL PORT

(71) Applicant: Medtronic Vascular, Inc., Santa Rosa, CA (US)

(72) Inventors: Adam Shipley, Santa Rosa, CA (US); Timothy Bertini, Santa Rosa, CA (US); Keith Perkins, Santa Rosa, CA (US); Gian Pellegrini, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 6 days.

(21) Appl. No.: 16/930,980

(22) Filed: Jul. 16, 2020

(65) Prior Publication Data

US 2022/0015891 A1   Jan. 20, 2022

(51) Int. Cl.
*A61F 2/07* (2013.01)
*A61F 2/06* (2013.01)

(52) U.S. Cl.
CPC .......... *A61F 2/07* (2013.01); *A61F 2002/061* (2013.01); *A61F 2002/065* (2013.01); *A61F 2002/067* (2013.01); *A61F 2002/068* (2013.01)

(58) Field of Classification Search
None
See application file for complete search history.

(56) References Cited

U.S. PATENT DOCUMENTS

| 9,034,027 B2 | 5/2015 | Ivancev | |
|---|---|---|---|
| 2014/0188207 A1* | 7/2014 | Havel | A61F 2/07 623/1.11 |
| 2018/0071076 A1* | 3/2018 | Guo | A61F 2/954 |

FOREIGN PATENT DOCUMENTS

| EP | 2 522 306 A1 | 11/2012 |
|---|---|---|
| EP | 2 564 812 A1 | 3/2013 |
| WO | 2018091464 A1 | 5/2018 |

OTHER PUBLICATIONS

International Search Report and Written Opinion dated Nov. 4, 2021 for PCT Appln. No PCT/US2021/040982 filed Jul. 9, 2021, 11 pages.

\* cited by examiner

*Primary Examiner* — Leslie Lopez
(74) *Attorney, Agent, or Firm* — Brooks Kushman P.C.

(57) ABSTRACT

A stent graft assembly with a sacrificial entry/exit port is disclosed. A first sacrificial port extends from a first branch stent graft and is configured to face a second branch stent graft when the stent graft assembly is in an expanded configuration. Likewise, a second sacrificial port can be provided, and can extend from the second branch stent graft and configured to face the first branch stent graft when the stent graft assembly is in the expanded configuration. The first and optional second sacrificial ports are configured to transition between (i) an open configuration to enable a guidewire or other surgical tool to pass from the first branch stent graft to the second branch stent graft while bypassing the main body, and (ii) a closed configuration to inhibit blood flow therethrough.

25 Claims, 17 Drawing Sheets

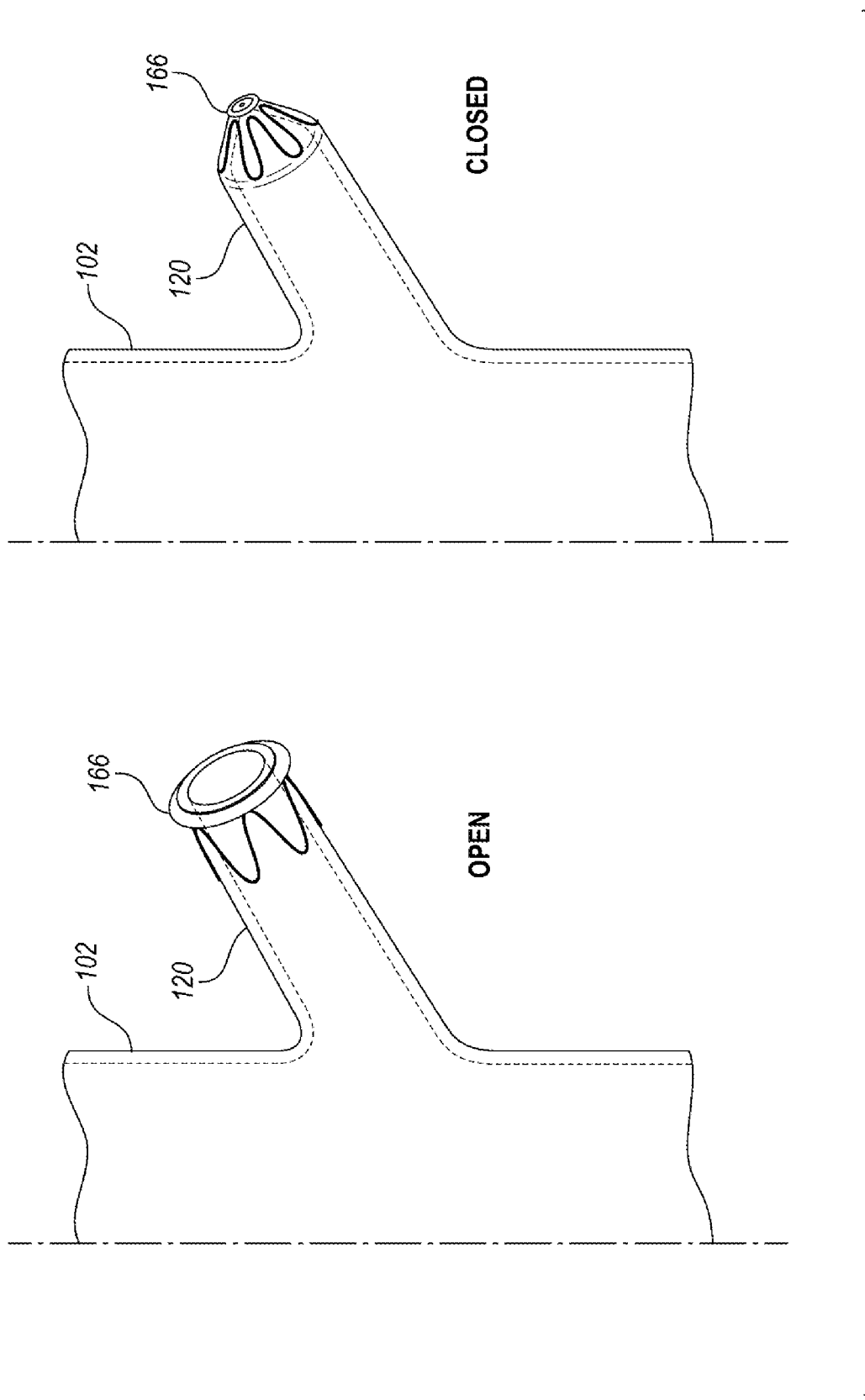

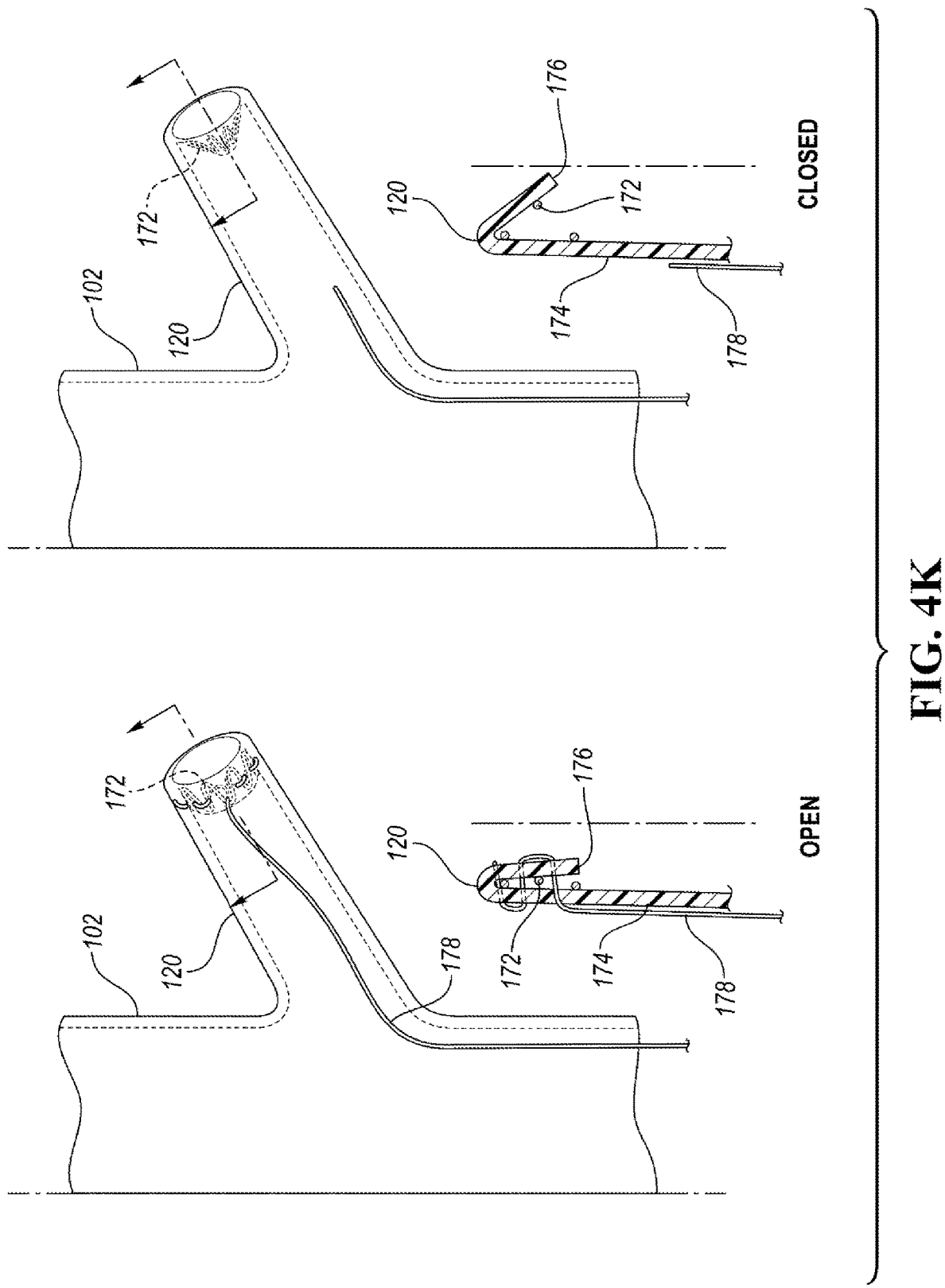

STENT GRAFT WITH SACRIFICIAL PORT

TECHNICAL FIELD

The present disclosure relates generally to a stent graft for a surgical (e.g., endovascular) procedure. In certain embodiments, the disclosure relates to a stent graft having a sacrificial entry/exit ports for allowing subsequently-delivered surgical devices.

BACKGROUND

Prostheses are implanted in blood vessels and other organs of living bodies. For example, prosthetic endovascular grafts constructed of biocompatible materials have been employed to replace or bypass damaged or occluded natural blood vessels. In general, endovascular grafts include a graft anchoring component that operates to hold a tubular graft component of a suitable graft material in its intended position within the blood vessel. The graft anchoring component typically includes one or more radially-compressible stents that are radially expanded in situ to anchor the tubular graft component to the wall of a blood vessel or anatomical conduit.

Rather than performing a traumatic and invasive open surgical procedure to implant a graft, endovascular grafts (e.g., stent grafts) may be deployed through a less invasive intraluminal delivery procedure. A lumen or vasculature may be accessed at a convenient and less traumatic entry point of the patient's body, and the stent graft may be routed through the vasculature to the site where the prosthesis is to be deployed. Intraluminal deployment typically uses a delivery catheter with tubes or shafts arranged for relative axial movement. For example, an expandable stent graft may be compressed and disposed within a distal end of an outer shaft of the delivery catheter fixed to an inner shaft. The delivery catheter may then be maneuvered, typically tracked through a body lumen until a distal end of the delivery catheter and the stent graft are positioned at the intended treatment site. The stent graft can then be deployed and radially expanded within the blood vessel.

SUMMARY

According to an embodiment, a stent graft assembly includes a stent graft having a main body, and first and second legs extending from the main body; a first branch stent graft extending from the first leg; a second branch stent graft extending from the second leg; a first sacrificial port extending from the first branch stent graft and configured to face the second branch stent graft when the stent graft assembly is in an expanded configuration; and a second sacrificial port extending from the second branch stent graft and configured to face the first branch stent graft when the stent graft assembly is in the expanded configuration. The first and second sacrificial ports are configured to transition between (i) an open configuration to enable a guidewire or other surgical tool to pass from the first branch stent graft to the second branch stent graft while bypassing the main body, and (ii) a closed configuration to inhibit blood flow therethrough.

According to an embodiment, a method of performing an endovascular aneurysm repair is provided. The method includes deploying a stent graft having a main body, and first and second legs extending from the main body; deploying a first branch stent graft extending from the first leg and having a first sacrificial port; deploying a second branch stent graft extending from the second leg such that a second sacrificial port faces the first sacrificial port; feeding a guidewire or other surgical tool into the first leg, then through the first sacrificial port, then through the second sacrificial port, and then into the second leg; removing the guidewire or other surgical tool from the first and second branch stent grafts; then closing the first sacrificial port and the second sacrificial port.

According to an embodiment, a system for performing an endovascular aneurysm repair includes a stent graft having a main body, a first leg extending from the main body and configured to direct toward a first artery, and a second leg extending from the main body and configured to direct toward a second artery; a sacrificial port extending from the main body and having a closure located at an end thereof; and a secondary stent graft delivery system configured to be delivered into the main body via the sacrificial port, and out through the first leg, while bypassing a length of the main body. The closure is configured to close the sacrificial port subsequent to removal of the secondary stent graft delivery system from the main body of the stent graft

BRIEF DESCRIPTION OF THE DRAWINGS

FIGS. 4C-4K illustrate various embodiments of methods of closing the sacrificial ports, with each embodiment shown in both an open configuration and a closed configuration.

DETAILED DESCRIPTION

Figure 1:
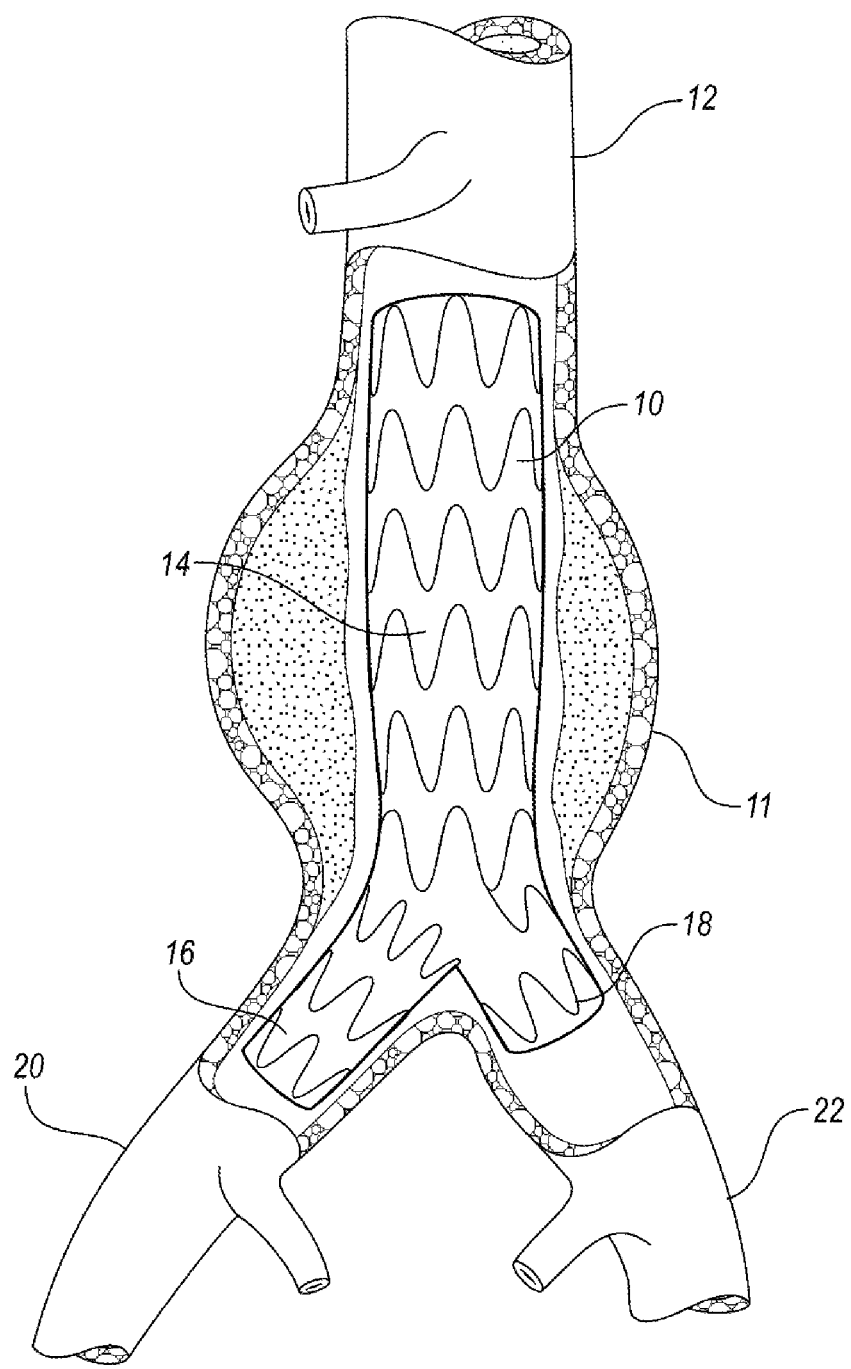
FIG. 1 is a side view of a stent graft installed into a blood vessel, for example an aorta, according to an embodiment.

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Directional terms used herein are made with reference to the views and orientations shown in the exemplary figures. A central axis is shown in the figures and described below. Terms such as "outer" and "inner" are relative to the central axis. For example, an "outer" surface means that the surfaces faces away from the central axis, or is outboard of another "inner" surface. Terms such as "radial," "diameter," "circumference," etc. also are relative to the central axis. The terms "front," "rear," "upper" and "lower" designate directions in the drawings to which reference is made.

Unless otherwise indicated, for the delivery system the terms "distal" and "proximal" are used in the following description with respect to a position or direction relative to a treating clinician. "Distal" and "distally" are positions distant from or in a direction away from the clinician, and "proximal" and "proximally" are positions near or in a direction toward the clinician. For the stent-graft prosthesis, "proximal" is the portion nearer the heart by way of blood flow path while "distal" is the portion of the stent-graft further from the heart by way of blood flow path.

The following detailed description is merely exemplary in nature and is not intended to limit the invention or the application and uses of the invention. Although the description is in the context of treatment of blood vessels such as the aorta, coronary, carotid and renal arteries, the invention may also be used in any other body passageways where it is deemed useful.

Endovascular stent grafting, or endovascular aneurysm repair (EVAR), is a form of treatment for abdominal or thoracic aortic aneurysm that is less invasive than open surgery. Endovascular stent grafting uses an endovascular stent graft to reinforce the wall of the aorta and to help keep the damaged area from rupturing by excluding the aneurysm from blood flow. Stent grafts are generally tubular open-ended structures providing support for damaged, collapsing, or occluded blood vessels, such as the aorta. Stent grafts are flexible, which allows them to be inserted through, and conform to, tortuous pathways in the blood vessels. For example, stent grafts may be radially expandable from a radially-compressed (or radially-constricted) configuration for delivery to the affected vessel site to a radially-expanded configuration when deployed at the affected vessel treatment site, with the radially-expanded configuration having a larger diameter than the radially-compressed configuration. Stent grafts may be inserted in the radially compressed configuration and expanded to the radially-expanded configuration either through a self-expanding mechanism, or through the use of a balloon catheter, for example.

In one example, an EVAR procedure may include inserting a guide wire into a portion of the patient's body, such as the femoral artery. Once the guidewire is inserted into the artery, it may be gently pushed toward the site of the aneurism. A stent graft delivery system, which may include a catheter and stent graft, may be placed over the guidewire and inserted along the guidewire into the site of the aneurism. The stent graft may be guided within the catheter in its radially-compressed configuration and to the site of the aneurism. There may be radiopaque markers at a distal end of the stent graft delivery system or on the stent graft itself to allow the surgeon to guide the stent graft into the proper position. Once in proper position, the stent graft can be expanded from the radially-compressed configuration to the radially-expanded configuration. This can be done, for example, by pulling back a stent-graft cover, allowing the stent graft to expand due to its fabric being biased outwards. Once deployed into the radially-expanded configuration, the stent graft can be held in place with metallic hooks or stents. The catheter can then be removed, while the stent graft remains.

FIG. 1 shows an example of a stent graft 10 in its installed, radially-expanded configuration within a blood vessel 12, in this case a patient's aorta, more particularly the abdominal aorta. Once affixed within the blood vessel 12, the stent graft 10 provides a tube or pipe for blood flow, guiding the blood flow through the stent graft 10. If the stent graft 10 is located within an aneurysm 11 of the blood vessel 12, the blood flow through the stent graft 10 may reduce the pressure within the aneurysm and allow it to reduce in size (regress) or remain stable. In one embodiment, graft material of the stent graft 10 is non-permeable, e.g., is polyester terephthalate (PET), expanded polyester terephthalate (ePET), polytetrafluoro-ethylene (PTFE), or other non-permeable graft material. As graft material is non-permeable, blood or other fluid is prevented from passing through graft material.

As shown in FIG. 1, the stent graft 10 may include main body 14, a first leg 16 extending from the main body 14, and a second leg 18 extending from the main body 14. The first leg 16 may be ipsilateral to where the initial guidewire was installed, and the second leg 18 that may be contralateral to the first leg 16, and may be shorter than the first leg 16. The first leg 16 may extend into or toward a first iliac artery 20, while the second leg 18 may extend into or toward a second iliac artery 22. The first and second legs 16, 18 may also guide blood flow therethrough, allowing those portions of the iliac arteries to heal, and removing stress from those regions of the arteries.

The first and second legs 16, 18 may be shorter than shown in FIG. 1, and may each provide a point of attachment for an additional stent graft that extends into the iliac arteries. Secondary stent grafts may subsequently be inserted within and attached to either or both of the first and second legs 16, 18 to elongate the overall profile of the stent graft. For example, once the initial stent graft 10 is deployed with the first leg 16 and second leg 18 extending toward their respective iliac arteries, a surgical physician may then attach secondary stent grafts to each respective leg 16, 18. Additional stent grafts may also be attached to these secondary stent grafts within the iliac arteries. To do so, the surgical physician may run a guidewire up the secondary stent graft attached to the first leg 16, through the first leg 16, into the main body 14 of the stent graft, and then down into the second leg 18, and through the secondary leg attached to the second leg 18.

Figure 2:
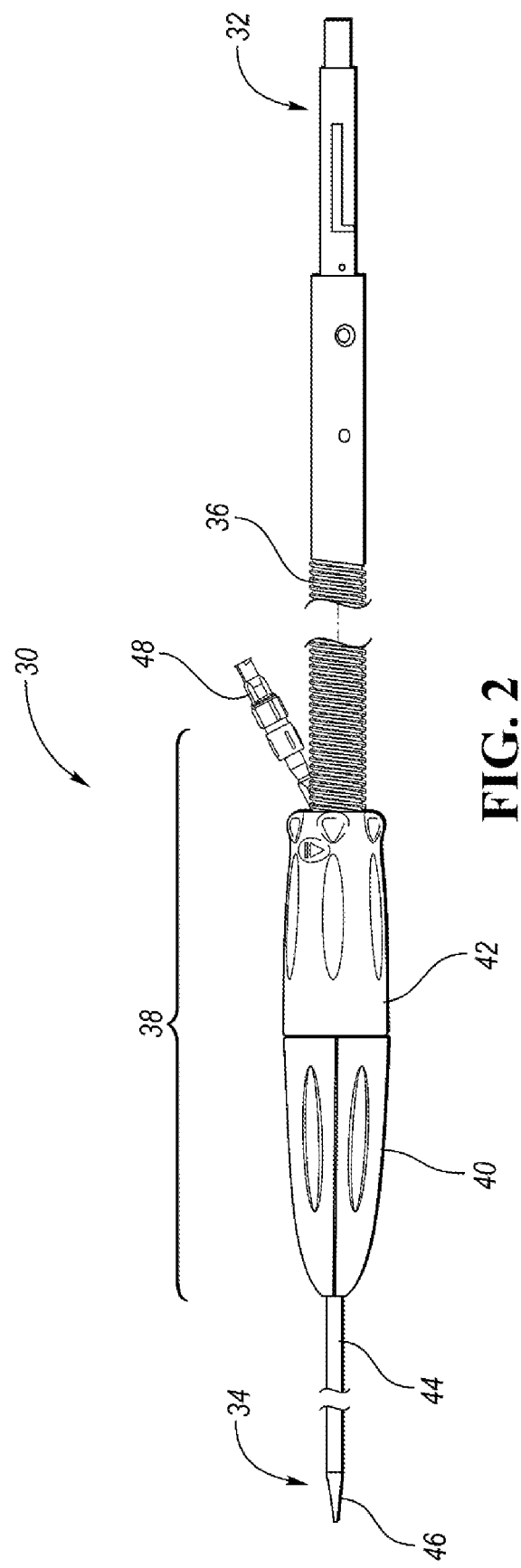
FIG. 2 is a schematic illustration of a stent graft delivery system, according to one embodiment.

FIG. 2 illustrates one embodiment of a stent graft delivery system 30. The stent graft delivery system 30 can be used to delivery and deploy a stent graft, such as the stent graft 10 of FIG. 1. In general, the stent graft delivery system 30 may include an endovascular catheter and extend between a proximal end 32 and a distal end 34. A threaded screw gear 36 extends along an axis between the proximal end 32 and the distal end 34. The threaded screw gear may be a multi-part shell configured to connect together to make a tubular screw gear. In one embodiment, the screw gear 36 is two half-shells configured to connect (e.g., snap or assemble) together. A handle assembly 38 is provided for grip by the clinician. The handle assembly 38 may include two separable portions, namely a front grip 40 and an external slider 42. The front grip 40 may be fixed relative to the screw gear 36, and the external slider 42 may rotate about a threaded outer surface of the screw gear 36 to move linearly along the screw gear 36. For example, during deployment of a stent graft, the external slider 42 is rotated to move toward the proximal end 32. Since the external slider 42 is operatively coupled to a stent graft cover 44 surrounding the stent graft (e.g., stent graft 10), the stent graft cover 44 is retracted with the linear movement of the external slider 42. Meanwhile, a tip 46 at the distal end 34 of the delivery system 30, which has openings to track over the guidewires, can remain steady within the vessel as the stent graft cover 44 is retracted away from the tip 46. Retraction of the stent graft cover 44 allows the stent graft to expand within the patient's vessel. Once the stent graft is deployed, the entire stent graft delivery system 30 may be retracted from the patent's vessel.

The stent grafts described herein can be self-expanding, in that it includes structures that are shaped or formed from a material that can be provided with a mechanical memory to return the structure from a compressed or constricted delivery configuration to an expanded deployed configuration. Each stent grafts can include two main components: a tubular graft, and one or more stents for supporting and expanding the graft. The graft may be formed from any suitable graft material, for example and not limited to, a low-porosity woven or knit polyester, DACRON material, expanded polytetrafluoroethylene, polyurethane, silicone, or other suitable materials. In another embodiment, the graft material can also be a natural material such as pericardium or another membranous tissue such as intestinal submucosa. The stent is radially-compressible and expandable, is coupled to the graft material for supporting the graft material, and is operable to self-expand into apposition with the interior wall of a body vessel (e.g., vessel 12) or another stent graft. Each stent can be constructed from a self-expanding or spring material, such as but not limited to Nitinol, stainless steel, a pseudo-elastic metal such as a nickel titanium alloy or nitinol, various polymers, or a so-called super alloy, which may have a base metal of nickel, cobalt, chromium, or other metal, or other suitable material. This allows the stent graft to expand when the stent graft cover 44 is retracted therefrom. The stent may be a sinusoidal patterned ring including a plurality of crowns or bends and a plurality of struts or straight segments with each crown being formed between a pair of opposing struts.

The stent graft delivery system 30 may also include an access port 48. The access port 48 provides an opening for insertion of a secondary guidewire lumen, or branching lumen, for surrounding a secondary guidewire. Once the secondary guidewire lumen is inserted, the delivery system 30 can track along both the main guidewire and the secondary guidewire during delivery of the stent graft. The access port 48 is optional; other stent graft delivery systems that are configured for delivering a non-branching stent graft may not include such an access port, and the delivery system may track along a single guidewire.

For complex aortic disease that encroaches vessels such as the iliac, a major barrier may be reducing procedural complexity while optimizing surgical implant performance. However, the procedure explained above can be complex at times. For example, the surgical physician may encounter various obstacles (e.g., blockages in the artery causing a contorted profile of the vessel) while attempting to feed the guidewire up one leg (e.g., leg 16), into the other leg (e.g., leg 18) of the stent graft.

Therefore, according to various embodiments described herein, a number of legs or stent grafts are provided with sacrificial entry/exit ports. The sacrificial ports may be on the first and and/or second legs, or on secondary stent grafts attached to each leg. The sacrificial ports may face one another, allowing the physician to add additional stent grafts to the stent-graft assembly without having to run a guidewire all the way up one leg, into the main body and then back down the other leg. Instead, the guidewire may be directed to exit one of the sacrificial ports of one leg, and enter one of the sacrificial ports of the other leg. This bypasses the main body of the stent graft, and provides a shorter distance of travel for the guidewire to reduce the complexity of going up and over the bifurcated stent graft to gain access to the desired vessel (e.g., the contralateral iliac artery).

Figure 3:
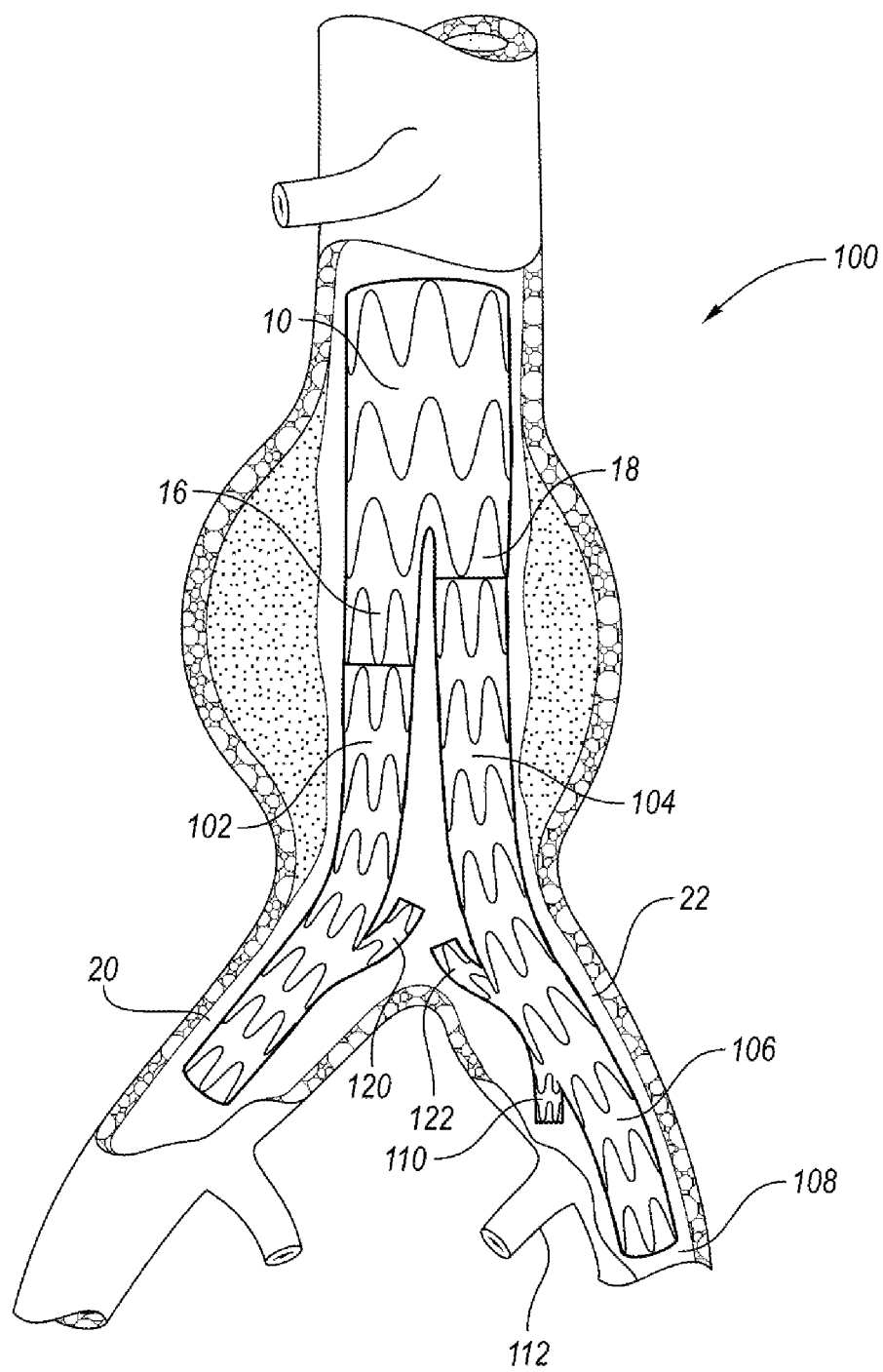
FIG. 3 is a side view of a stent graft assembly installed into a branched artery, in which the stent graft assembly includes two stent grafts each having a sacrificial port, according to one embodiment.

FIG. 3 illustrates an example of a stent graft assembly 100 in an installed, radially-expanded configuration within a blood vessel 12, e.g., a proximal portion of an abdominal aorta. The stent graft assembly 100 includes the branched stent graft 10 explained above. Alternatively, the stent graft assembly 100 can be provided with various other types or configurations of stent grafts. FIG. 3 once again shows an embodiment in which the stent graft 10 has a first leg 16 extending toward a first iliac artery 20, and a second leg 18 extending toward a second iliac artery 22.

The stent graft assembly 100 also includes a first branch stent graft 102 assembled to and extending from a distal end of the first leg 16, and a second branch stent graft 104 assembled to and extending from a distal end of the second leg 18. Each of the first branch stent graft 102 and the second branch stent graft 104 can have similar material and structural makeup as the stent graft 10 explained above. In one embodiment, a proximal end of the first branch stent graft 102 is delivered within the first leg 16 and expanded to couple (e.g., fasten, hook, latch, etc.) to a distal end of an inner wall of the first leg 16. The same process can be done for the second branch stent graft 104 within the second leg 18. In an alternative embodiment, the first branch stent graft 102 is continuous and part of the first leg 16 and delivered therewith, and/or the second branch stent graft 104 is continuous and part of the second leg 18 and delivered therewith.

Upon deployment, the first branch stent graft 102 may extend into the first iliac artery, and the second branch stent graft 104 may extend into the second iliac artery 22. Each branch stent graft 102, 104 may also have legs or portions that extend into tributary vessels of the patient's vasculature. For example, in the embodiment shown in FIG. 3, the second branch stent graft 104 includes a portion or leg 106 that extends further into the second iliac artery 22 or a tributary vessel 108. The second branch stent graft 104 may also include a portion or leg 110 that extends toward, but not into, another tributary vessel 112 (e.g., internal iliac artery). The portion or leg 110 may provide an access port for access and delivery of additional stent grafts into that tributary vessel 112. Likewise, the portion or leg 106 may provide an access port and attachment point for access and delivery of additional stent grafts into that tributary vessel 108.

One or both of the branch stent grafts 102, 104 may include sacrificial entry/exit ports. For example, the first branch stent graft 102 may include a first sacrificial entry/exit port 120, and the second branch stent graft 104 may include a second sacrificial entry/exit port 122. These sacrificial ports are sized and configured to receive a guidewire therethrough for tracking and delivery of a surgical device of another delivery system.

Figure 4A:
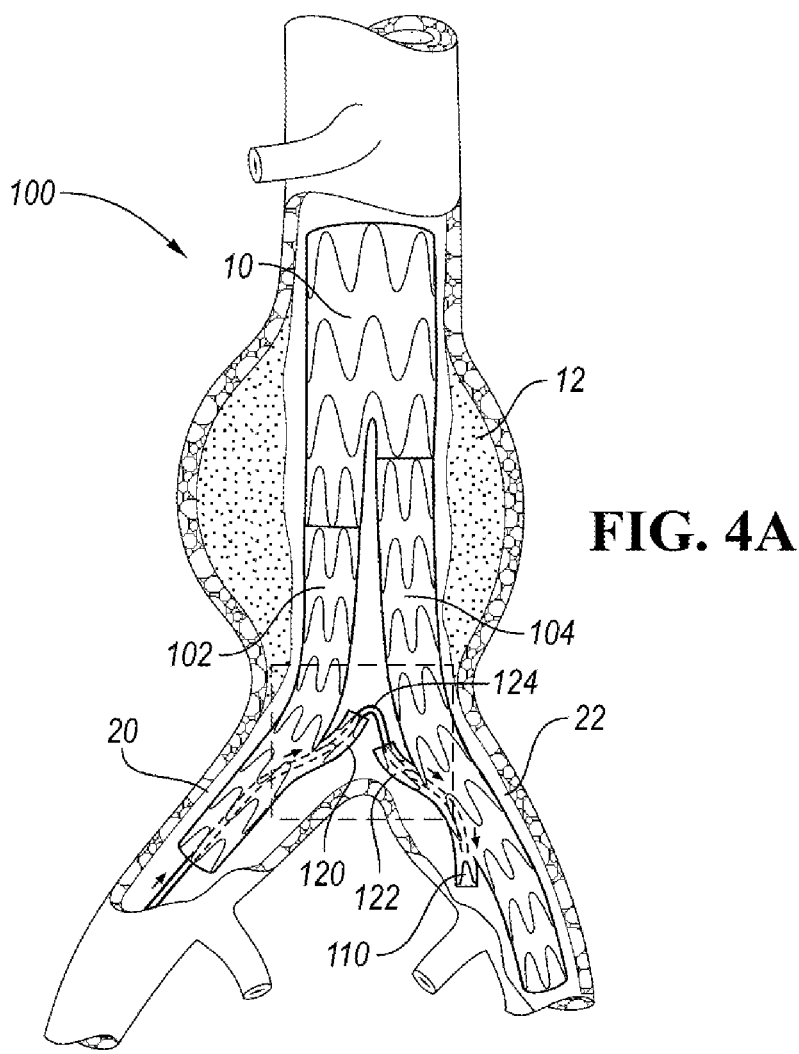
FIG. 4A is a side view of the stent graft assembly of FIG. 3 with a guidewire passing from one sacrificial port of one stent graft to another sacrificial port of another stent graft, according to one embodiment.

FIG. 4A illustrates the use of the sacrificial ports 120, 122 for delivering a guidewire 124 from the first stent graft 102 to the second branch stent graft 104. This configuration allows the guidewire 124 to reach a destination (e.g., second iliac artery 22) without having to travel up and into the stent graft 10, or at least the main body 14 thereof. In this embodiment, the first sacrificial port 120 is an exit port as the guidewire 124 exits the first branch stent graft 102 therethrough, and the second sacrificial port 122 is an entry port as the guidewire 124 enters the second branch stent graft 104 therethrough.

As shown in FIG. 4A, the first branch stent graft 102 and second branch stent graft 104 may be positioned such that the respective sacrificial ports 120, 122 face one another. For example, both ports may face medially or towards the sagittal plane. In one embodiment, the exit port may be configured to be above (e.g., superior or cranial) the entry port. These relative positions may facilitate the exit of the guidewire 124 through the first sacrificial port 120 at a location that is adjacent to the second sacrificial port 122 to minimize a length of travel of the guidewire 124.

Figure 4B:
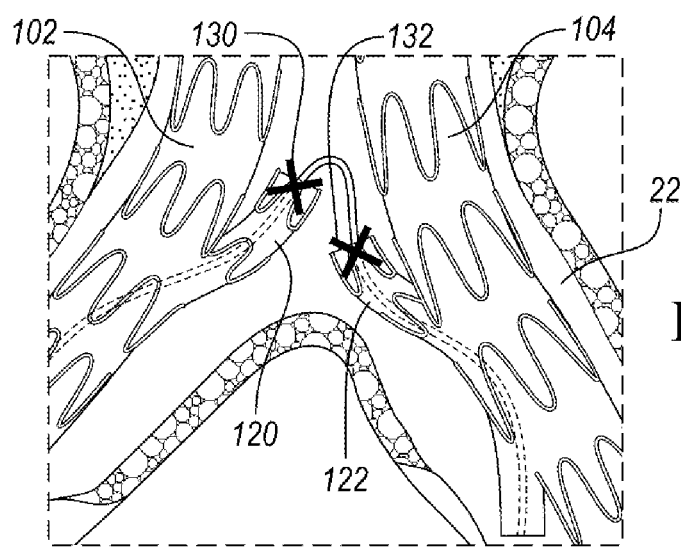
FIG. 4B is an enlarged view of a region of FIG. 4A, with the guidewire removed and the sacrificial ports subsequently closed, according to one embodiment.

As also shown in FIGS. 4A-4B, the opening of each port 120, 122 may face generally proximally (i.e., upstream toward the heart) so that the guidewire 124 can exit the first sacrificial port in a direction that is generally aligned with the direction that the guidewire 124 is fed into the patient. Once the guidewire 124 is fed beyond the first sacrificial port 120, the guidewire 124 can then be bent to change direction to be fed the distal direction (e.g., downstream away from the heart) whereupon it enters the proximally-facing second sacrificial port 122. However, in other embodiments, the ports may face in different proximal/distal directions. For example, the exit port may face generally distally while the entry port faces generally proximally. This configuration may allow the guidewire to be aligned or generally aligned with the entry port as it exits the exit port, which may facilitate easier cannulation of the entry port. In this configuration, the exit port may be configured to be above (e.g., superior or cranial) the entry port.

Each sacrificial port 120, 122 may include extensions of material (e.g., graft material) of the respective branch stent grafts, and may be supported by reinforcement structures such as stent structures. The graft material of the sacrificial ports 120, 122 may extend from fenestrations or openings in the branch stent grafts to define a lumen therethrough. The graft material of the ports may be formed integrally or seamlessly with the branch stent graft (e.g., during the material weaving process) or the components maybe formed separately and secured together (e.g., with sutures). In certain embodiments, each sacrificial port 120, 122 has a self-expanding reinforcing ring at its internal and/or external end to maintain the port in an open configuration. Other embodiments of opening and closing the sacrificial ports 120, 122 are described below. External ends of each sacrificial port 120, 122 may be provided with a radiopaque marker to facilitate the exit and entrance of the guidewire therethrough.

Once the guidewire 124 has passed through the sacrificial ports 120, 122, a delivery system (not shown) may be tracked along the guidewire 124 and into the desired location, e.g., into the second iliac artery 22. Once there, this delivery system may deploy another stent graft, or other surgical tool. The delivery system and guidewire 124 can then be retracted.

After the sacrificial ports 120, 122 have been used for this delivery of the guidewire 124 and tracking procedure/deployment, it may be desirable to close the sacrificial ports 120, 122. Closing these ports 120, 122 assures blood is directed through the stent graft assembly 100, and does not travel into the regions between the stent graft assembly 100 and the vessel 12 itself. This allows the stent graft assembly 100 to properly contain the flow of blood therein, allowing the aneurism to heal.

FIG. 4B shows the sacrificial ports 120, 122 closed, as represented by respective general closures 130, 132. The closures 130, 132 can include one or more of many potential mechanics for closing the ports 120, 122. In one embodiment, at least one of the closures 130, 132 includes a pull wire that, when pulled by the guidewire or other surgical instrument, cinches the external end of the port closed. In yet another embodiment, at least one of the closures 130, 132 includes an inwardly-biased ring that, when broken or otherwise activated by the guidewire or other surgical instrument, contracts and closes. At least one of the closures 130, 132 may be biased open, whereupon a force can be applied to the closure to occlude the respective port 120, 122 after use of the ports 120, 122. In addition, or alternatively, at least one of the closures 130, 132 may be biased closed, whereupon a force can be applied (e.g., inserting a delivery system) to open the closure for use of the ports 120, 122 and removal of the force (e.g., withdrawing a delivery system) causes the closures to return to a closed state.

FIGS. 4C-4K illustrate various embodiments of the closure 130 of the sacrificial port 120, with various mechanisms for closing the port 120. In each of these Figures, there is an "open" view in which the sacrificial port 120 is open (e.g., for passing a guidewire 124 or delivery system therethrough as explained above), and a "closed" view in which the sacrificial port 120 has been subsequently closed to inhibit blood flow therethrough. While sacrificial port 120 is shown in each of these Figures, it should be understood that identical or similar structure can be provided in the other sacrificial port 122 with its respective closure 132. Alternatively, ports 120 and 122 may use different closure mechanisms, which may be mixed and matched from those disclosed herein.

Figure 4C:
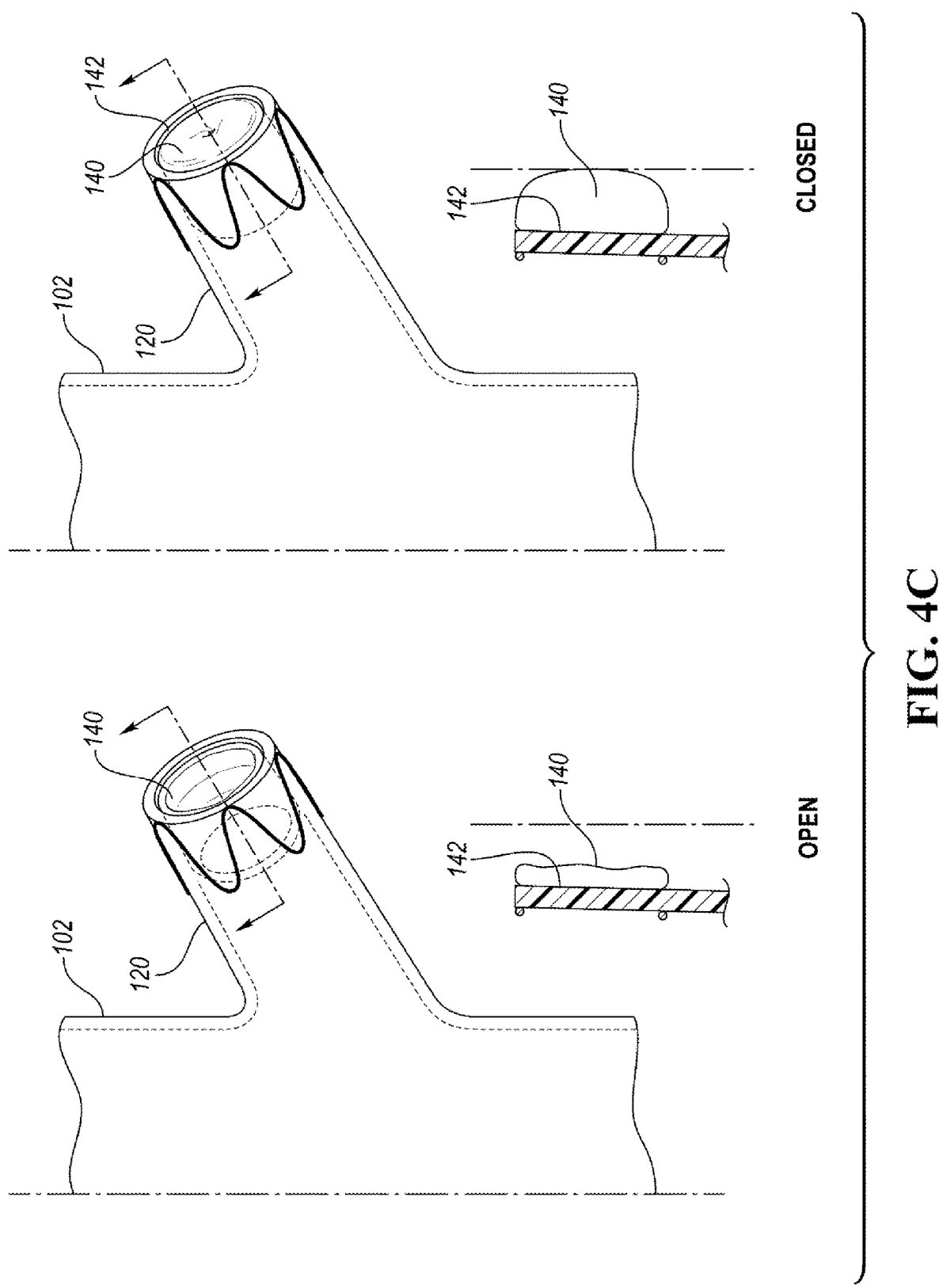

In an embodiment illustrated in FIG. 4C, an internal sack or ring 140 can be coupled to an internal wall 142 of the port 120. The ring 140 can be inflated (e.g., with saline) to expand inwardly to close off the port 120. The inflatable ring can be elastic. Excessive inflatable material can be provided initially in the ring that accommodates and facilitates the entry/exit of the guidewire 124 and associated delivery system due to a vacuum or absence of fluid in the ring prior to closure of the port 120.

Figure 4D:
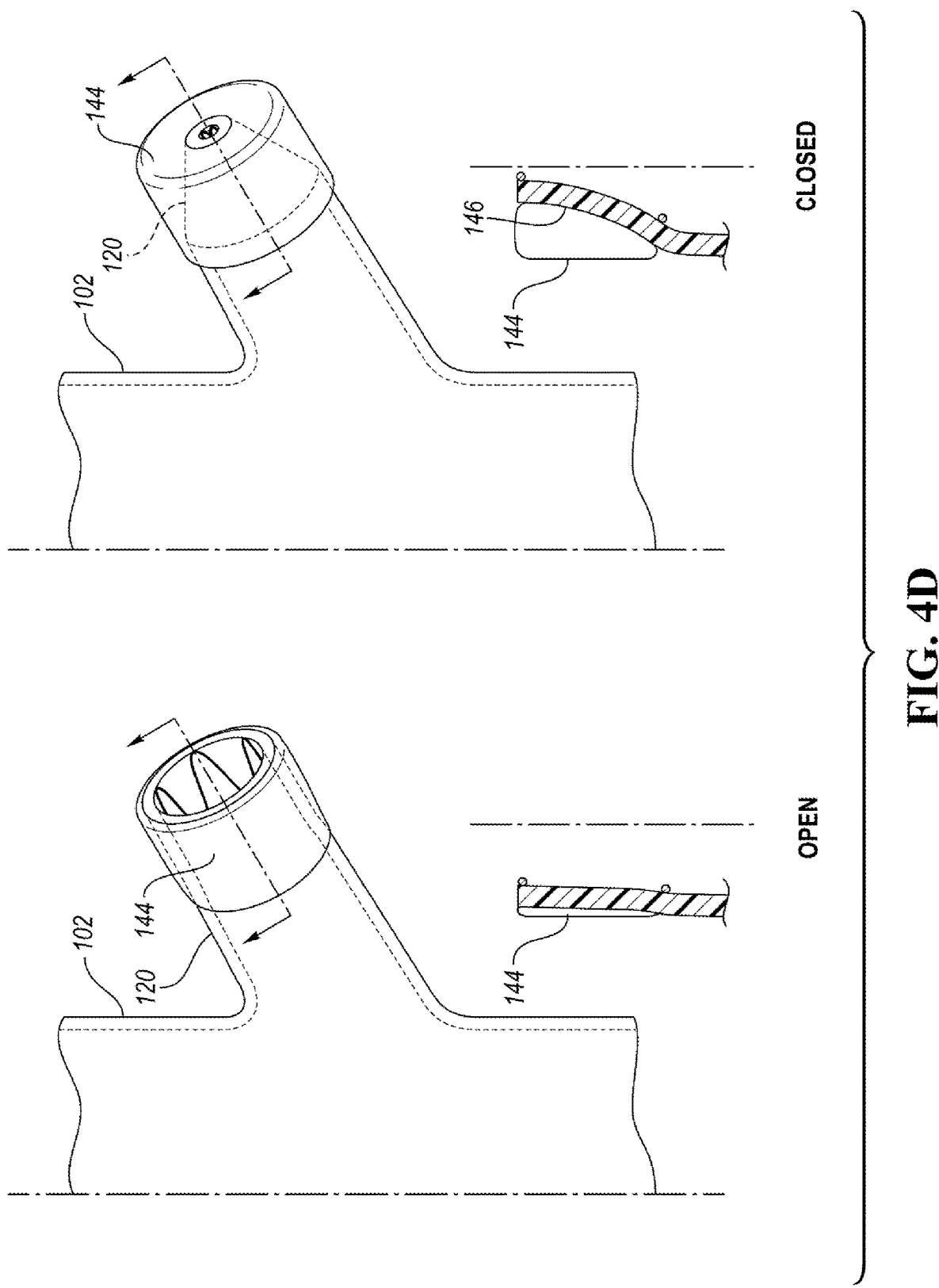

In an embodiment illustrated in FIG. 4D, an external ring 144 can be provided about an external surface 146 of the port 120. Similar to the embodiment of FIG. 4C, the external ring 144 can be inflated (e.g., with saline). This compresses the port 120 inwardly to close the port 120. The embodiments shown in FIGS. 4C and 4D may include an inflation lumen that is connected to a source of fluid (e.g., saline) in order to inflate the ring. The inflation lumen may be similar to those used in inflatable medical balloons (e.g., for angioplasty).

Figure 4E:
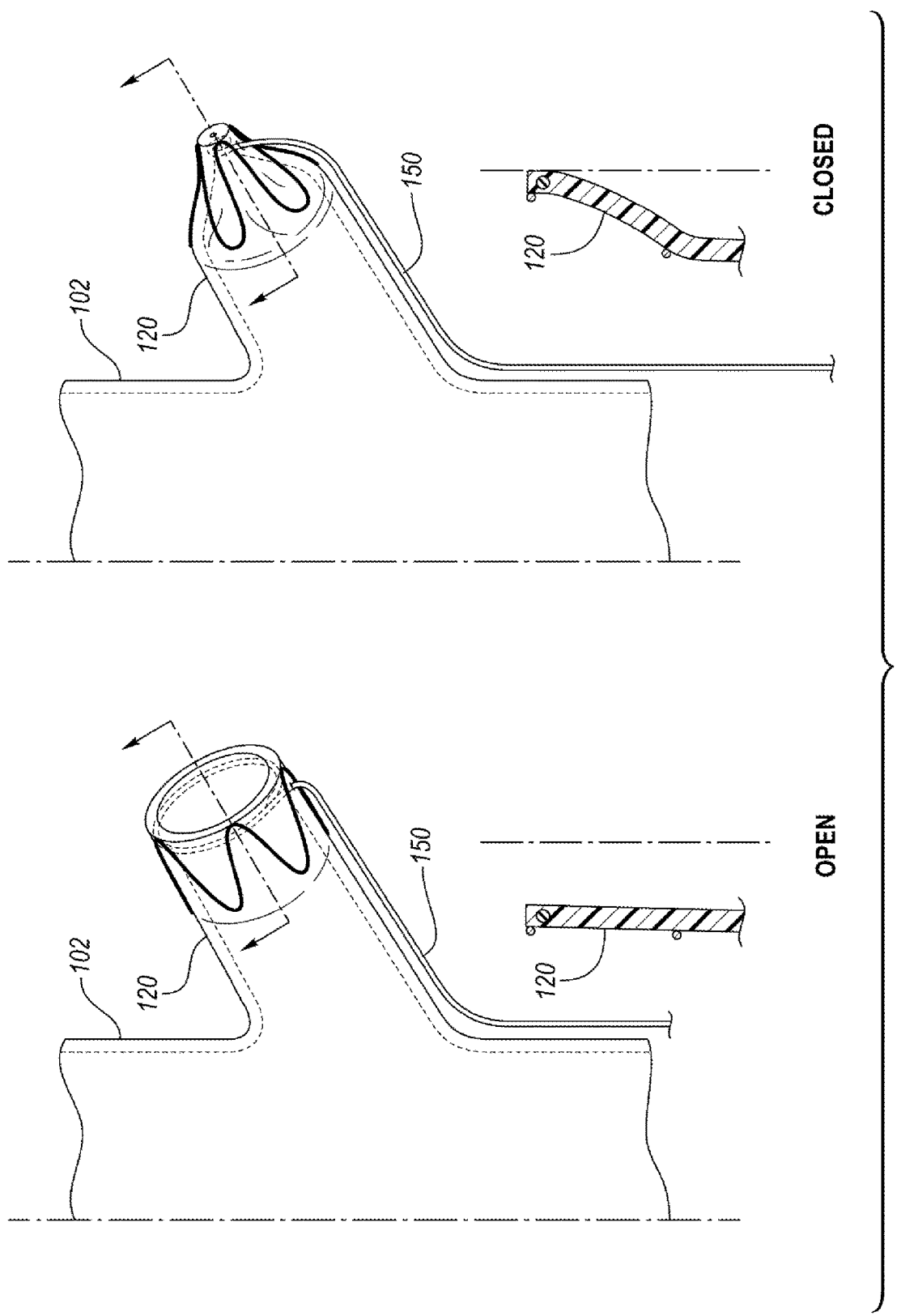

In an embodiment illustrated in FIG. 4E, a pull wire or string 150 wraps around the port 120 and extends outwardly therefrom. The pull wire or string can extend out of the patient's body, or at least to an additional tool within the patient's body. The surgical technician or tool can apply tension to the pull wire or string, collapsing the port 120.

The port 120 can either be biased open or biased closed, and a pull wire or string can be used to either close the biased-open port or open the biased-closed port. In one embodiment, a knot (e.g., slip knot, hitch knot, etc.) can be used to secure the pull wire or string about the port 120, and pulling of the wire or string can untie or release the knot, allowing the port 120 to open via the stent at the port 120 that is biased to close. In another embodiment, other closures besides knots can be employed. For example, a staple- or plug-based closure can secure the suture in the closed configuration.

Figure 4F:
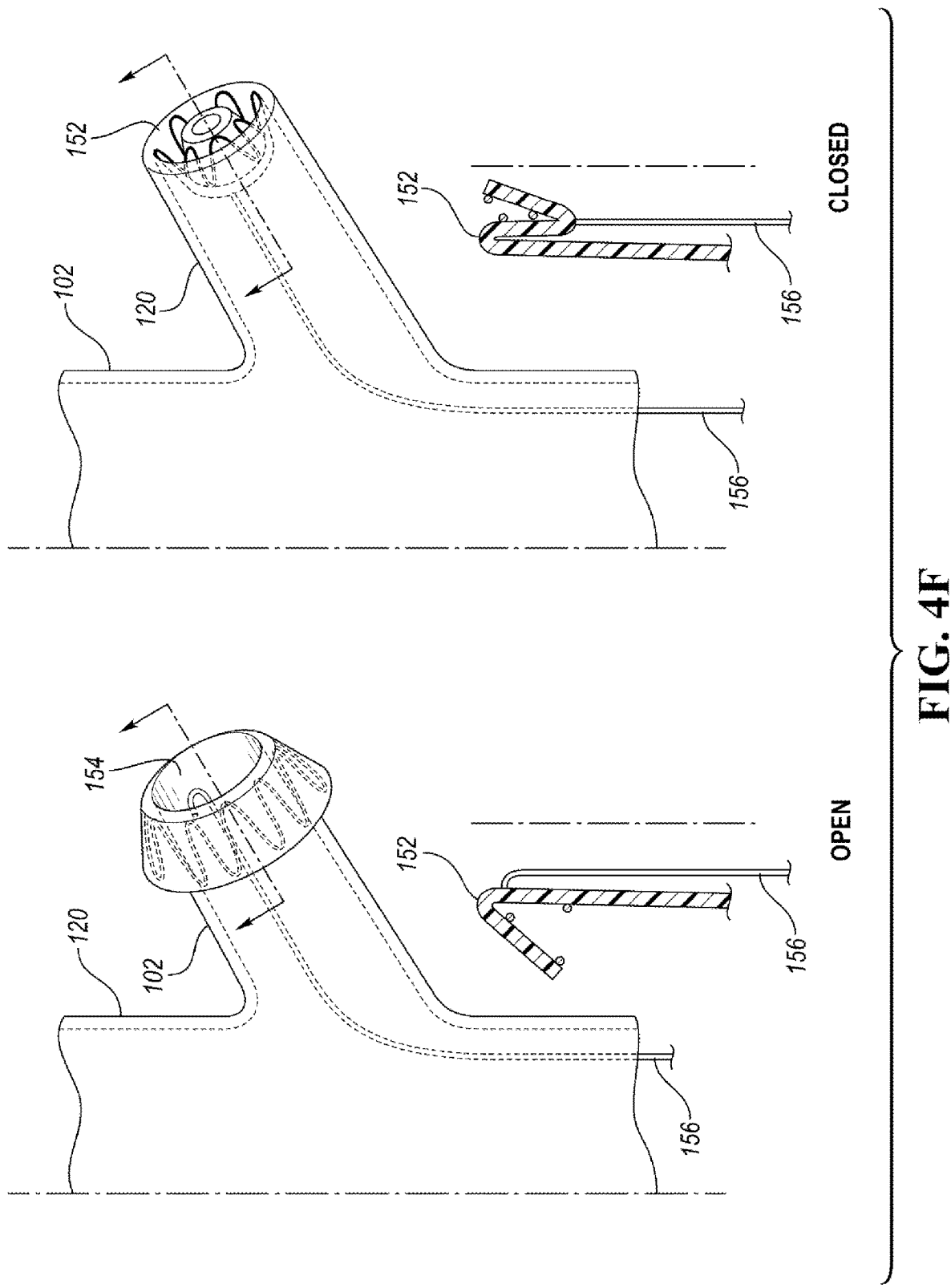

In an embodiment illustrated in FIG. 4F, the end of the port 120 may be provided with a stent 152. The stent may have alternating peaks. The stent may be oversized compared to its respective port 120. Alternating stent peaks can be attached to the port and another ring 154 of material can be attached to the stent peaks that expands outwardly. The addition of the ring 154 of material can be a continuation of the fabric of the graft material of the port 120, folded back over the exterior of the port 120 at a larger diameter than the opening of the port. A wire 156 or string can run along the interior surface of the port 120 to the surgical technician, whereupon the technician can pull tension on the wire 156 or string to cause the stent end of the port to invert. This results in the stent peaks of the ring 154 to close off the port 120.

Figure 4G:
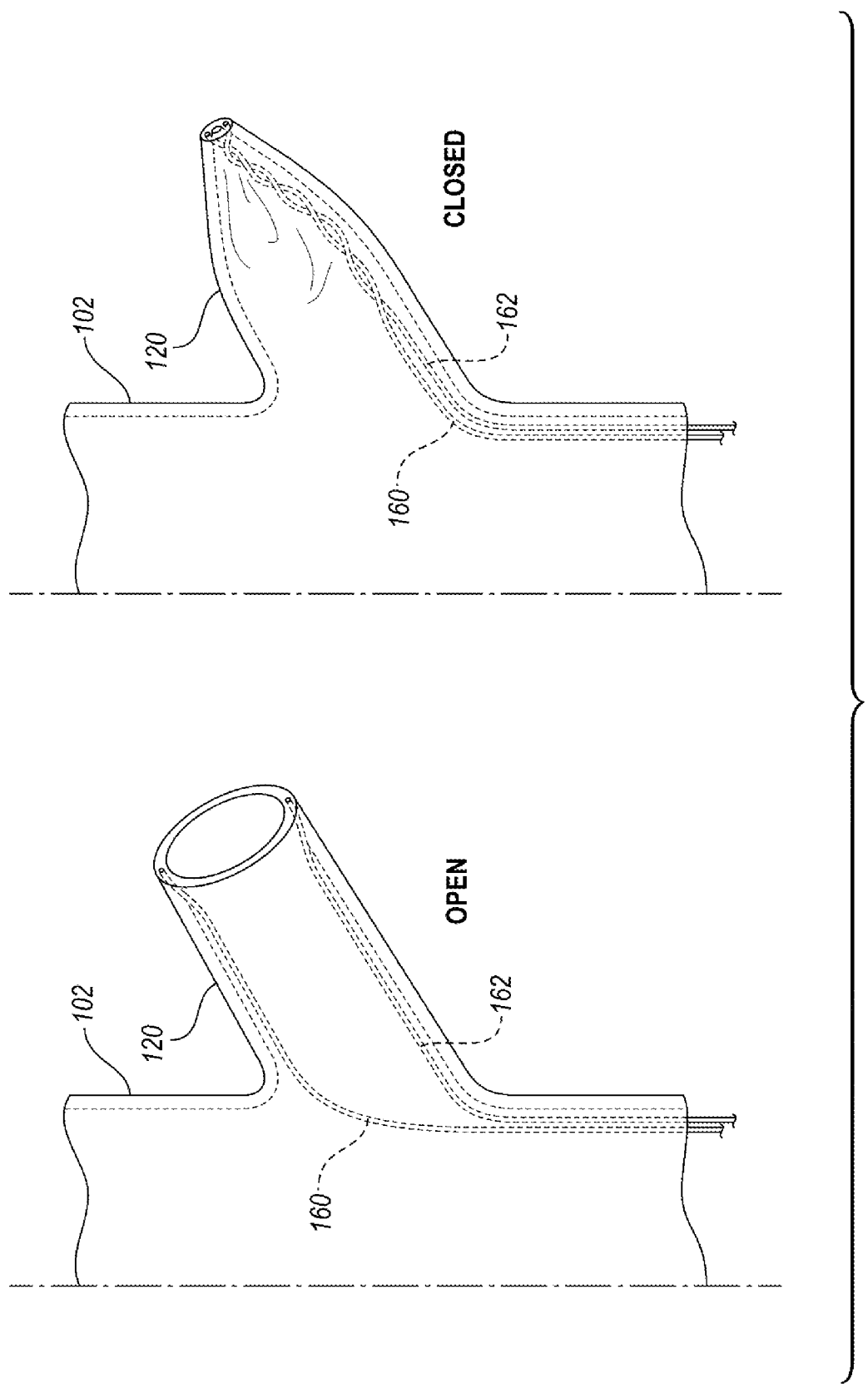

In an embodiment illustrated in FIG. 4G, two wires 160, 162 or strings can be attached to opposing sides of the opening of the port 120, and run back to the surgical technician. The technician can twist the wires or strings to correspondingly twist the port 120, causing it to collapse. The two wires 160, 162 or strings at the port 120 can then be tied in a knot to secure the closure of the port 120.

Figure 4H:
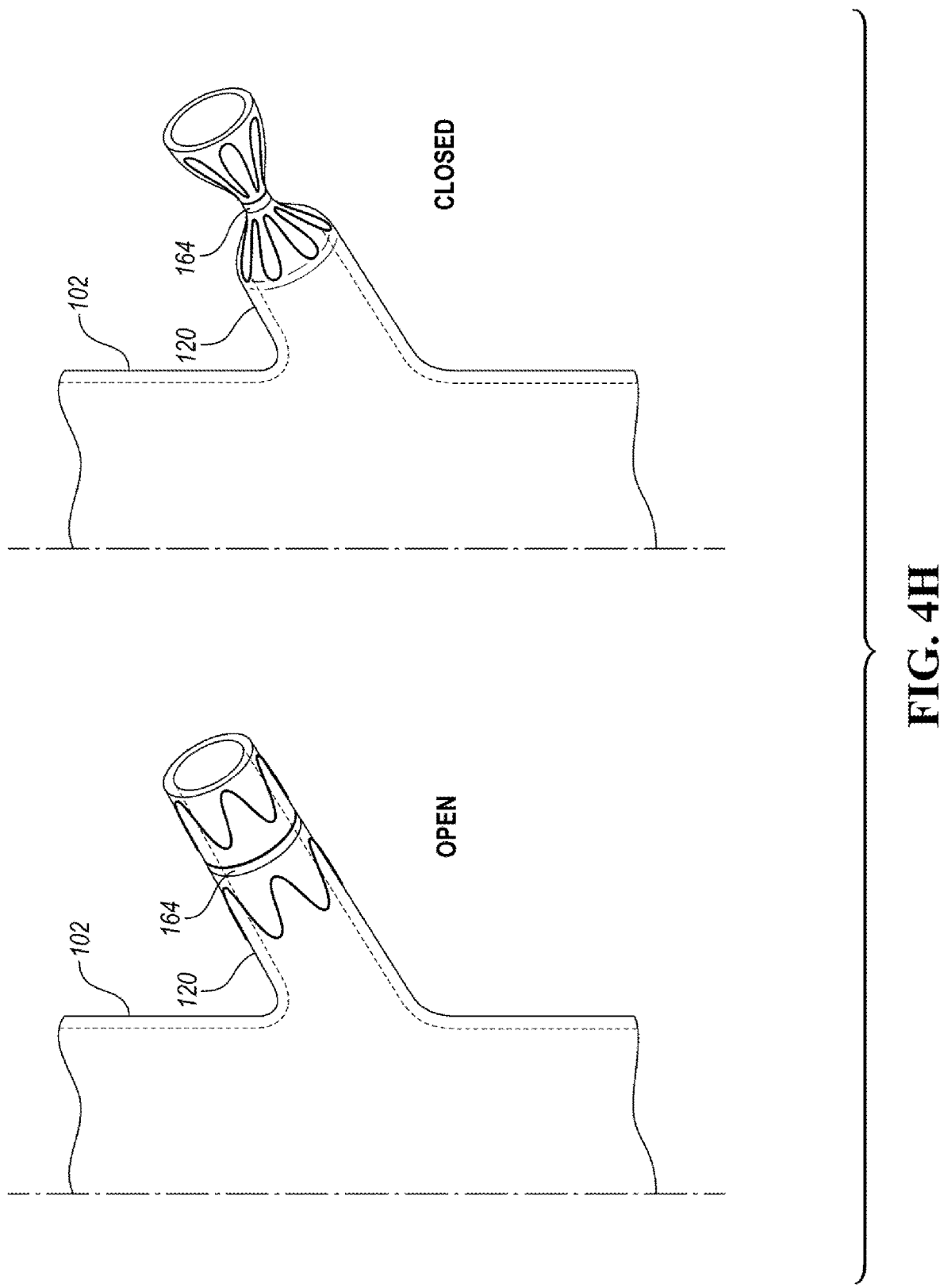

In an embodiment illustrated in FIG. 4H, a piece of elastic material 164 (e.g., ring, string, strip, etc.) may wrap about the port 120. The elastic material 164 may be biased in its closed position to close the port, but expands when a delivery system or accessory is placed through it. When the delivery system or accessory is removed, the elastic material 164 returns to its natural shape to close the port. While only one piece of elastic material 164 is shown, in other embodiments there could be several pieces of elastic material at spaced-apart locations along the port 120.

In an embodiment illustrated in FIG. 4I, an elastic ring 166 is provided about the port 120 at an end thereof. The ring 166 may be inflatable with fluid (e.g., saline). In its normal configuration without being inflated, the ring 166 may be closed, and providing fluid to the ring 166 may expand the ring 166 and the attached port 120 to the open configuration. An inflation lumen and source may be provided, as described above.

Figure 4J:
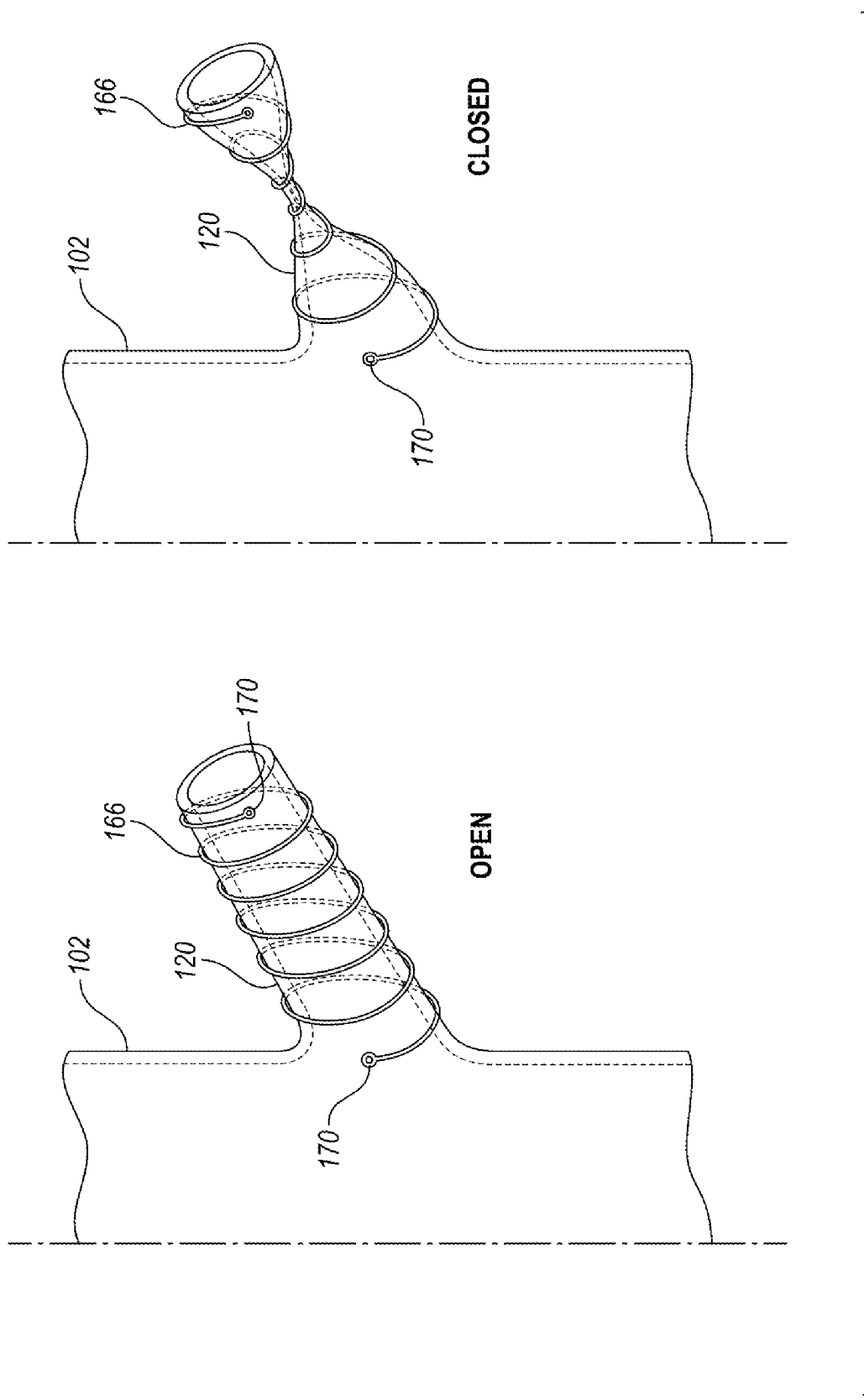

In an embodiment illustrated in FIG. 4J, a spiral wire 168 extends about the exterior of the port 120 and has a loop 170 at either end. The spiral wire 168 in its natural state collapses the port 120, but when the spiral wire 168 is rotated against its spiral direction, the port 120 is expanded to open. The spiral wire 168 can be rotated to open the port 120, and a stiff wire (not shown) can be placed through the two loops 170 of the spiral wire 168 to prevent the spiral wire from rotating back and closing the port 120. Once the stiff wire is removed, the spiral wire 168 is biased to rotate back to its natural state to collapse the port 120.

In an embodiment illustrated in FIG. 4K, the port 120 is provided with an internal stent 172 having alternating stent peaks. The internal stent 172 is attached to an external graft material 174 and an internal graft material 176. The internal graft material 176 can be a separate piece or a continuation of the external graft material 174. At least one of the proximal peaks of the internal stent 172 is biased to collapse in, and can be held open by suturing or tying it via suture 178 to the external graft material. The suture 178 can be pulled to remove from the port 120, resulting in the internal graft material 176 and peaks of the internal stent 172 collapsing inward.

In another embodiment, the port 120 may be provided with an envelope of material containing a hydroscopic material (e.g., hydrogel) that absorbs liquid from blood and swells within the envelope. Therefore, the ports 120, 122 may be initially inserted into the patient in a contracted position, and absorption of blood within the envelopes over time gradually closes the ports 120, 122. Generation of hydrostatic pressure within the envelope closes off the opening at a predictable and tunable rate.

In another embodiment, the ports 120, 122 may be closed via a delivery of a secondary occlusion device over the guidewire after manipulation through the ports 120, 122 is complete. The secondary occlusion device may be used to selectively occlude the respective port 120, 122 itself. The secondary occlusion device may be a covered stent-based or coil/Nitinol mesh-based occlusion system. The secondary occlusion device may be deployed into the corresponding port 120, 122, or if the port 120, 122 is a simple fenestration, the secondary occlusion device can be a rivet structure.

In another embodiment, the closure of the ports 120, 122 can be performed via delivery of a secondary stent graft cuff that walls off the port from the luminal (e.g., interior) side of the graft after manipulation through the port 120, 122 is complete.

At least one of the closures 130, 132 may be biased closed, whereupon a force can be applied to open the closures temporarily for the delivery of the guidewire 124 and associated delivery system. In one embodiment, a piece of elastic material (e.g., a string or stent around the end of each port 120, 122) can be biased in a collapsed configuration to maintain the closures 130, 132 closed. These pieces of material can be forced to expand when a guidewire or delivery system is placed therethrough.

In another embodiment, a spiral wire extends about the exterior of each port 120, 122, and each spiral wire has a loop at either end. Each spiral wire in its natural state collapses the ports 120, 122, but when the spiral is rotated against its spiral direction, the ports 120, 122 are expanded to open. The spiral wire can be rotated to open the ports 120, 122, and a stiff wire can be placed through the two loops of each spiral wire to prevent the spiral wire from rotating back and closing the respective port 120, 122. Once the stiff wire is removed, the spiral wire is biased to rotate back to its natural state to collapse the associated port.

Figure 5A:
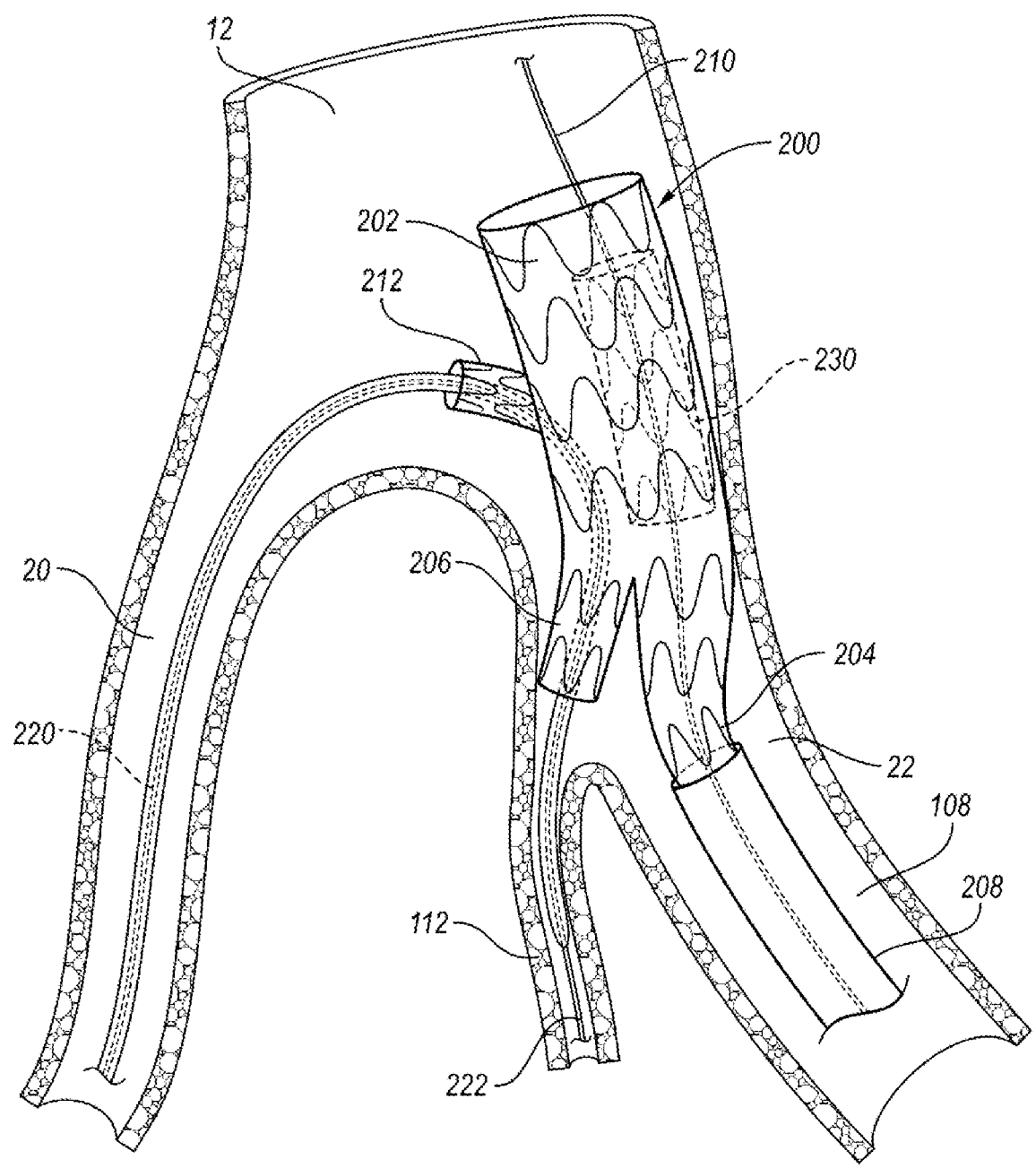
FIG. 5A is a side view of a stent graft assembly installed into a branched artery, according to another embodiment in which a guidewire and delivery system is fed into a sacrificial port of one stent graft, and out through a leg of that stent graft, with an internal cuff in a constricted configuration.
Figure 5B:
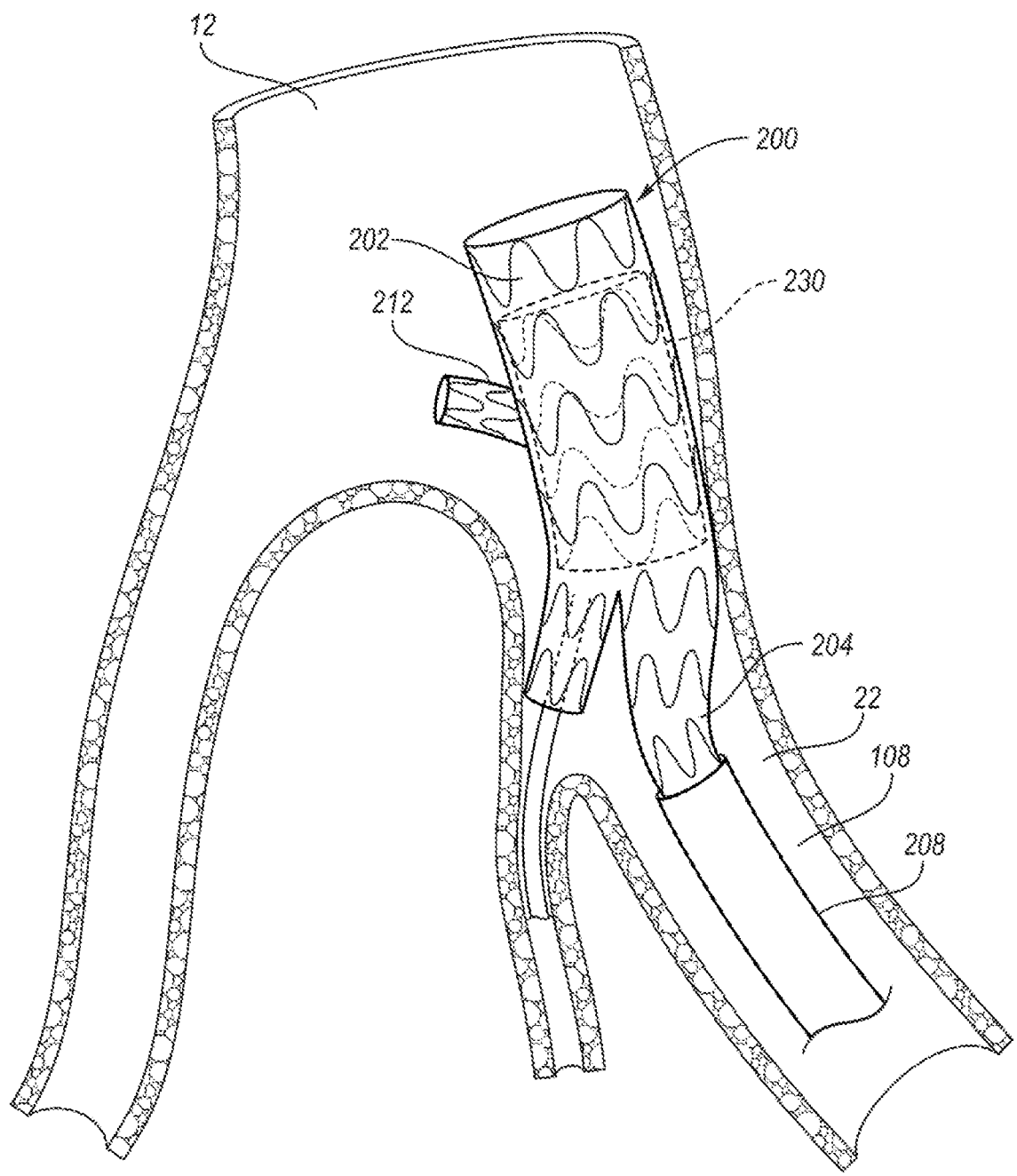
FIG. 5B is a view similar to FIG. 5A, with the guidewire and delivery system removed, and the internal cuff in an expanded configuration.

FIGS. 5A-5B show another embodiment of a stent graft assembly, in which a staged deployment is utilized to block off a sacrificial port once the port has served its purpose. In this embodiment, an internal cuff within the stent graft can be released as part of a staged deployment that walls off the sacrificial port of the stent graft from the luminal side once the sacrificial port has served its purpose of allowing access through the stent graft.

Referring to FIG. 5A, a stent graft assembly 200 is shown within a blood vessel 12, e.g., a proximal portion of an abdominal aorta. The stent graft assembly 200 includes a first stent graft or main stent graft 202. The main stent graft 202 is shown to be partially deployed within the abdominal aorta, specifically within the second (e.g., left) iliac artery 22. The main stent graft 202 may be a branched stent graft, such as those described above, with a first leg or main leg 204 extending further into a main portion 108 of the iliac artery 22, and a second leg 206 extending in a direction toward a tributary vessel 112 (e.g., internal iliac artery). It should be understood that the vessels shown in FIGS. 5A-5B are merely exemplary, and the teachings of the stent graft assembly 200 described herein can be applied to other vessels throughout the body. As shown in FIGS. 5A and 5B, a stent graft cover 208 covers a portion of the main leg 204 to not allow the main leg 204 to fully deploy. In other embodiments, the stent graft cover 208 is removed so that the main leg 204 is in its fully-deployed configuration within the iliac artery 22.

Referring to FIG. 5A, a guidewire 210 extends through the main stent graft 202 for delivery thereof. The stent graft cover 208 and associated delivery system tracks along this guidewire 210. The main stent graft 202 also has a sacrificial entry/exit port 212. This port 212 can be formed of the structure described in embodiments above. For example, the sacrificial port 212 can be an extension of graft material of the stent graft 202, can have its own stents or elastic members, can have a collapsible ring on its outer edge, or other embodiments described above. In short, the sacrificial port 212 can be similar to the sacrificial ports 120, 122 described above. The sacrificial port 212 can also have its own closure that operates similar to the closures 130, 132 described in the various embodiments above. Additional disclosure of closing the sacrificial port 212 is provided below.

The sacrificial port 212 provides access to a secondary stent graft delivery system 220. The secondary stent graft delivery system 220 can extend along its own dedicated guidewire 222. During operation, the guidewire 222 can be fed from the first iliac artery 20, into the sacrificial port 212, and down into the second leg 206. The secondary stent graft delivery system 220 can then track along this guidewire 222 to a desired deployment location within the vessel 112 (e.g., internal iliac artery).

The sacrificial port 212 reduces the required length of travel of the guidewire 222 and secondary stent graft delivery system 220. Instead of traveling all the way up to the proximal opening of the stent graft 202, entrance into the stent graft 202 can be made through the sacrificial port 212 which can be located adjacent the second leg 206, or closer to the second leg 206 than the proximal opening of the stent graft 202. Said another way, the sacrificial port 212 allows the secondary stent graft delivery system to enter the main body of the stent graft 202 while bypassing the length of the main body of the stent graft located more proximal (e.g., up, in the orientation of FIG. 5A) of the sacrificial port 212.

As mentioned above, the sacrificial port 212 can be closed similar to the methods described above with reference to closures 130, 132. However, FIGS. 5A-5B illustrate an additional method of closing the sacrificial port 212. This embodiment can likewise be applied to the stent graft assemblies of previous embodiments.

In this embodiment, the stent graft assembly 200 is provided with an internal cuff 230. The internal cuff 230 may be a stent graft, having a graft material as a main body and one or more stents extending about the graft material for self-expanding, similar to other stent grafts explained herein. The internal cuff 230 can remain in a constricted, undeployed, or semi-deployed configuration as shown in FIG. 5A while the secondary stent graft delivery system 220 is passed through the stent graft 202 and into the vessel 112. This provides clearance within the stent graft 202 so that the internal cuff 230 does not interfere with the delivery of the secondary stent graft delivery system 220 through the stent graft 202.

After the secondary stent graft delivery system 220 has properly delivered a stent graft or performed other necessary functions, the delivery system 220 can be removed through the sacrificial port 212. Subsequently, the sacrificial port 212 can be closed. One embodiment of closing the sacrificial port 212 is shown in FIG. 5B. In this embodiment, the internal cuff 230 is expanded outwardly to an expanded configuration within the stent graft 202 such that the internal cuff 230 covers the sacrificial port 212. This inhibits blood in the vessel 12 from entering or exiting the stent graft 202 through the sacrificial port 212. This also provides additional structural support to the stent graft 202 from within. In one embodiment, the cuff 230 is a stent graft that is biased to expand to a size radially equal to or greater than the main stent graft 202, thus providing a force against the interior surface of the stent graft 202 to properly close and seal the sacrificial port 212. Another way to expand the internal cuff 230 outwardly is to perform a staged deployment procedurally. Rather than building in a second unified stent that is released as part of the deployment, the sacrificial port can be closed with a bridging stent that connects the stent graft 202 to a bifurcated stent graft (not shown). In that embodiment, the bridging stent can dock into the bifurcated stent graft and extend to a location just distal to the sacrificial port 212, closing it off from circulation. The distal end of the bridging stent can end just prior to the proximal portion of the sacrificial port 206, thus maintaining the patency of the branch.

As shown and explained with reference to FIGS. 5A-5B, the internal cuff 230 can be deployed in stages. For example, in FIG. 5A, the internal cuff 230 may be only partially deployed, and in FIG. 5B, the internal cuff 230 may be fully deployed. Such a staged deployment can be performed in a plurality of embodiments, two of which are shown in FIGS. 6A-6B and 7A-7B.

Figure 6B:
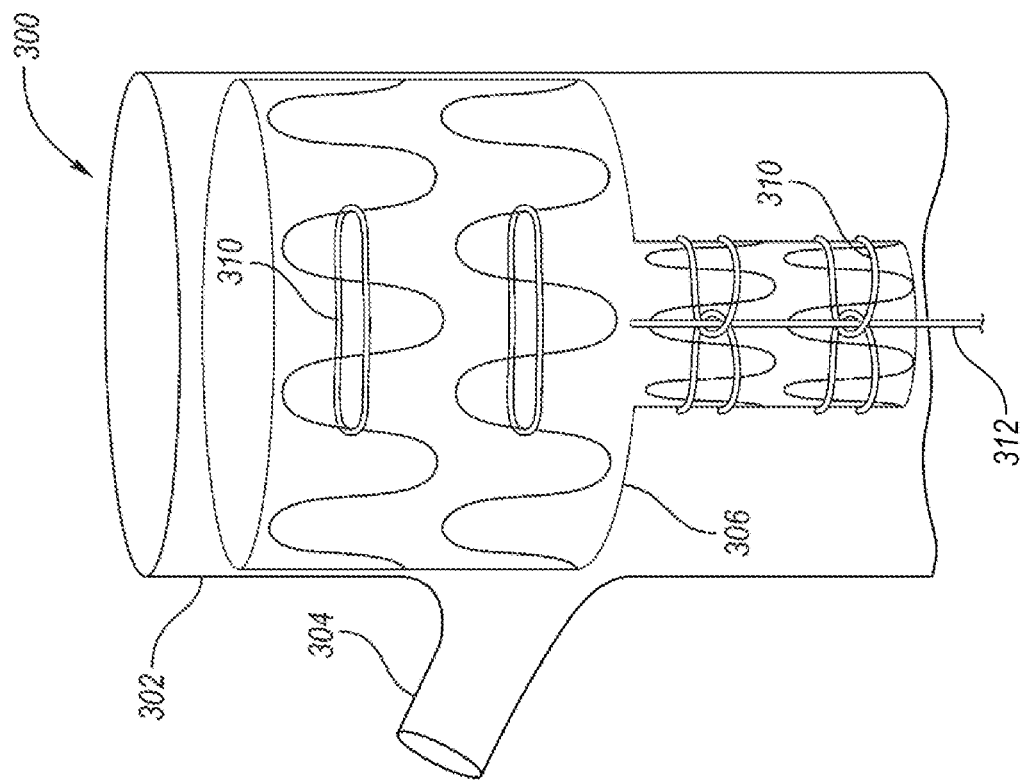
FIGS. 6A and 6B illustrate a staged-deployment system for closing a sacrificial port of a stent graft, according to one embodiment.
Figure 6A:
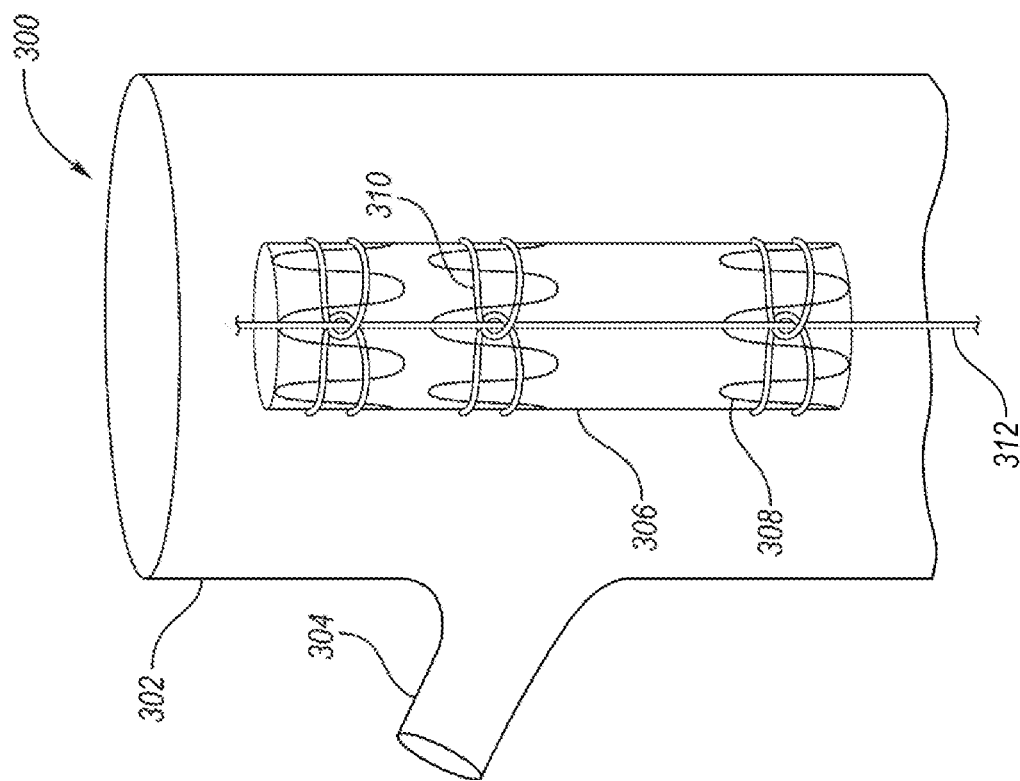

FIGS. 6A-6B illustrate one embodiment of a staged-deployment system 300 for closing a sacrificial port of a stent graft. The system includes a general stent graft 302 with a sacrificial port 304, which can be similar to embodiments explained above such as stent graft 202 and sacrificial port 212. In other words, the teachings of the staged-deployment system 300 can be implemented into various embodiments above, such as those described with reference to FIGS. 5A-5B.

The staged-deployment system 300 includes an internal cuff 306, which may be an expandable stent graft made of a graft material and having a plurality of stents 308 biased to expand the stent graft radially outwardly. One or more suture loops 310 may be attached to the graft material of the internal cuff 306. The suture loops 310 are configured to constrain the stents 308 such that the internal cuff 306 is maintained in a constricted configuration. The suture loops 310 may each be looped about itself, such that two looped ends are attached with each looped end extending through the other looped end (e.g., like a chain). A trigger wire or release wire 312 extends through looped ends of the suture loops 310, keeping the suture loops 310 closed and preventing the expansion of the stents 308.

As the release wire 312 is pulled out of the internal cuff 306, the looped ends of the suture loops 310 are free to separate, thus allowing the stents 308 to expand. This is shown in FIG. 6B. As the internal cuff 306 is allowed to expand, it covers the sacrificial port 304 to block blood flow therethrough. As used herein, the term suture loops may refer to surgical sutures, but also may include any wire, thread, or filament type structure (e.g., not limited only to surgical sutures).

Figure 7A:
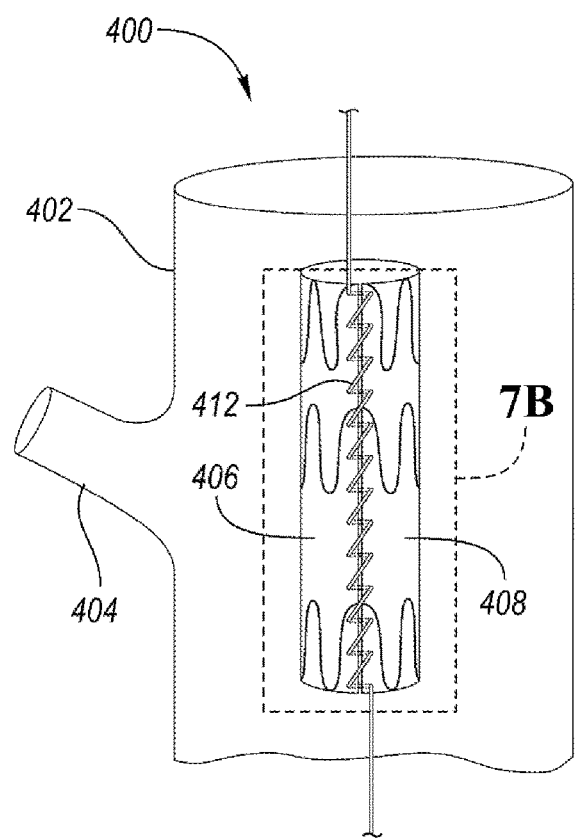
FIGS. 7A and 7B illustrate a staged-deployment system 00 for closing a sacrificial port of a stent graft, according to another embodiment.
Figure 7B:
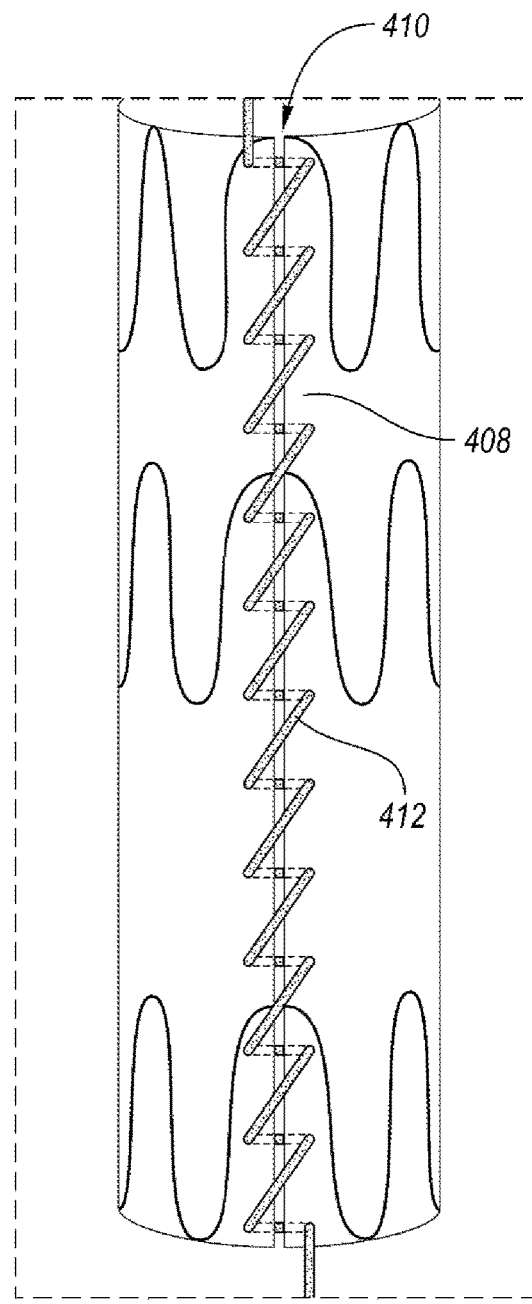

FIGS. 7A-7B illustrate another embodiment of a staged-deployment system 400 for closing a sacrificial port of a stent graft. Once again, the system includes a general stent graft 402 with a sacrificial port 404, which can be similar to embodiments explained above such as stent graft 202 and sacrificial port 212. In other words, the teachings of the staged-deployment system 400 can be implemented into various embodiments above, such as those described with reference to FIGS. 5A-5B.

The staged-deployment system 400 includes an internal cuff 406 which, once again, can be an internal stent graft located within the main stent graft 402. A sheath or cover 408 may be provided about the internal cuff 406 to keep the cuff 406 in a constricted configuration. The cover 408 may be made of a pliable material such as, for example, the same material as the graft material of the stent grafts described herein. The cover 408 may be discontinuous, in that it is not a single, uninterrupted piece of material that surrounds the internal cuff 406. Instead, the cover 408 may have a gap 410 between two ends thereof.

A removeable suture 412 (e.g., wire, thread, or filament type structure) may be used to tie the two ends of the cover 408 together, thus constraining the internal cuff 406 therein. The suture 412 may be threaded through the gap 410 of the cover 408. Removal of the suture allows the ends of the cover 408 to separate, thus allowing the internal cuff 406 to expand to an expanded configuration and close off the sacrificial port 404. The internal cuff 406 may be removed with the removeable suture or by a separate mechanism (e.g., a dedicated tether). Alternatively, the cuff may be pinned to the main graft wall by the cuff during its expansion.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A stent graft assembly comprising:
a stent graft having a main body, and first and second legs extending from the main body;
a first branch stent graft extending from the first leg;
a second branch stent graft extending from the second leg;
a first sacrificial port extending from the first branch stent graft when the stent graft assembly is in an expanded configuration;
a second sacrificial port extending from the second branch stent graft when the stent graft assembly is in the expanded configuration; and
a closure wrapped about the first sacrificial port and configured to close the first sacrificial port,
wherein each of the first and the second sacrificial ports have:
an open configuration to enable a guidewire or other surgical tool to pass from the first branch stent graft to the second branch stent graft while going around the main body, and
a closed configuration to inhibit blood flow therethrough.

2. The stent graft assembly of claim 1, further comprising a pull wire configured to, when pulled, transition at least one of the first or the second sacrificial ports from the open configuration to the closed configuration.

3. The stent graft assembly of claim 1, wherein the closure includes an elastic material biased to close the first sacrificial port.

4. The stent graft assembly of claim 1, wherein the first sacrificial port is configured to face the second branch stent graft when the stent graft assembly is in the expanded configuration.

5. The stent graft assembly of claim 4, wherein the second sacrificial port is configured to face the first branch stent graft when the stent graft assembly is in the expanded configuration.

6. The stent graft assembly of claim 1, wherein the closure includes a sack coupled to an internal wall of the first sacrificial port, wherein the sack is configured to inflate with a fluid to expand within and close the first sacrificial port.

7. The stent graft assembly of claim 1, wherein the closure includes a sack coupled to an exterior wall of the first sacrificial port, wherein the sack is configured to inflate with a fluid to expand in order to close the closure.

8. The stent graft assembly of claim 1, wherein the closure includes an invertible ring at an end of the sacrificial port, and the stent graft assembly includes a pull wire connected to the ring, wherein pulling of the pull wire inverts the invertible ring to close the first sacrificial port.

9. The stent graft assembly of claim 1, further comprising a first wire attached to a first side of an end of the first sacrificial port, and a second wire attached to a second side of the end of the first sacrificial port, wherein twisting of the wires forces the first sacrificial port to close.

10. The stent graft assembly of claim 1, wherein the closure includes a spiral wire biased to close the first sacrificial port, wherein twisting of the spiral wire opens the first sacrificial port.

11. A stent graft assembly comprising:
a stent graft having a main body, and first and second legs extending from the main body;
a first branch stent graft extending from the first leg;
a second branch stent graft extending from the second leg;
a first sacrificial port extending from the first branch stent graft when the stent graft assembly is in an expanded configuration; and
a second sacrificial port extending from the second branch stent graft when the stent graft assembly is in the expanded configuration,
wherein the first sacrificial port and the second sacrificial port are configured to face proximally when the stent graft assembly is in the expanded configuration,
wherein each of the first and the second sacrificial ports have:

an open configuration to enable a guidewire or other surgical tool to pass from the first branch stent graft to the second branch stent graft while going around the main body, and a closed configuration to inhibit blood flow therethrough.

12. The stent graft assembly of claim 11, wherein the first and second sacrificial ports include first and second openings, respectively, and the first opening is configured to permit the guidewire to exit the first sacrificial port in an exit direction aligned with a feeding direction in which the guidewire is fed into a patient.

13. A stent graft assembly comprising:
a stent graft having a main body extending along a longitudinal axis, and first and second legs extending from the main body;
a first branch stent graft extending from the first leg and having proximal and distal ends;
a second branch stent graft extending from the second leg and having proximal and distal ends;
a first sacrificial port extending from the first branch stent graft between the proximal and distal ends of the first branch stent graft and having a first opening when stent graft assembly is in an expanded configuration; and
a second sacrificial port extending from the second branch stent graft between the proximal and distal ends of the second branch stent graft and having a second opening when stent graft assembly is in the expanded configuration;
wherein each of the first and the second openings of the first and the second sacrificial ports, respectively, face the longitudinal axis of the main body.

14. The stent graft assembly of claim 13, wherein the first branch stent graft includes a first branch stent graft tubular side extending between the proximal and distal ends of the first branch stent graft when stent graft assembly is in the expanded configuration, and the first sacrificial port extends from the first branch stent graft tubular side to the first opening when stent graft assembly is in the expanded configuration.

15. The stent graft assembly of claim 14, wherein the first sacrificial port includes a first sacrificial port tubular side extending between the first branch stent graft tubular side and the first opening.

16. The stent graft assembly of claim 14, wherein the first opening is located above the second sacrificial port when stent graft assembly is in the expanded configuration.

17. The stent graft assembly of claim 13, wherein the first opening is configured to exit a guidewire or another surgical tool.

18. The stent graft assembly of claim 13, wherein both of the first sacrificial port and the second sacrificial ports extend medially the stent graft assembly when stent graft assembly is in the expanded configuration.

19. The stent graft assembly of claim 13, wherein both of the first and the second sacrificial ports extend toward a sagittal plane when stent graft assembly is in the expanded configuration.

20. A stent graft assembly comprising:
a stent graft having a main body, and first and second legs extending from the main body;
a first branch stent graft extending from the first leg;
a second branch stent graft extending from the second leg;
a first sacrificial port extending from the first branch stent graft; and
a second sacrificial port extending from the second branch stent graft;
wherein the first and the second sacrificial ports are configured, when the stent graft assembly is in an expanded configuration within a blood vessel, to transition from:
an open configuration to enable a guidewire or other surgical tool to pass from the first branch stent graft to the second branch stent graft while bypassing the main body, and
a closed configuration to inhibit blood flow therethrough.

21. The stent graft assembly of claim 20, further comprising a pull wire configured to, when pulled, transition at least one of the first or the second sacrificial ports from the open configuration to the closed configuration.

22. The stent graft assembly of claim 20, wherein the first branch stent graft includes a first branch stent graft tubular side extending between the proximal and distal ends of the first branch stent graft, and the first sacrificial port extends from the first branch stent graft tubular side to a first opening.

23. The stent graft assembly of claim 22, wherein the first sacrificial port includes a first sacrificial port tubular side extending between the first branch stent graft tubular side and the first opening.

24. The stent graft assembly of claim 23, further comprising a closure wrapped about a middle portion of the first sacrificial port tubular side and configured to close the first sacrificial port.

25. The stent graft assembly of claim 20, further comprising a closure wrapped about the first sacrificial port and configured to close the first sacrificial port.

* * * * *